United States Patent

Matsunaga et al.

[11] Patent Number: 6,080,755
[45] Date of Patent: Jun. 27, 2000

[54] 1,9-DIAZABICYCLO[4.3.0]NONA-3,8-DIENE DERIVATIVES

[75] Inventors: Hiroshi Matsunaga, Kawagoe; Souiti Kaneda, Shiki; Hisashi Shimidzu, Niiza; Yoshiyuki Shikata, Asaka; Toshio Kumagai, Kawagoe, all of Japan

[73] Assignee: Wyeth Lederle Japan, Ltd., Japan

[21] Appl. No.: 09/000,415

[22] PCT Filed: Aug. 5, 1996

[86] PCT No.: PCT/JP96/02192

§ 371 Date: Feb. 3, 1998

§ 102(e) Date: Feb. 3, 1998

[87] PCT Pub. No.: WO97/06168

PCT Pub. Date: Feb. 20, 1997

[30] Foreign Application Priority Data

Aug. 7, 1995 [JP] Japan ................................. 7-219453

[51] Int. Cl.[7] ...................... A61K 31/437; A61K 31/496; C07D 221/00; C07D 471/04
[52] U.S. Cl. ........................ 514/300; 514/210; 514/233.2; 514/253; 546/121; 544/127; 544/362
[58] Field of Search .................. 546/121; 514/300, 514/210, 233.2, 253; 544/127, 362

*Primary Examiner*—Richard L. Raymond
*Assistant Examiner*—Ann Kessinger
*Attorney, Agent, or Firm*—Testa, Hurwitz & Thibeault, LLP

[57] ABSTRACT

Disclosed are diazabicyclo compounds of formula (I)

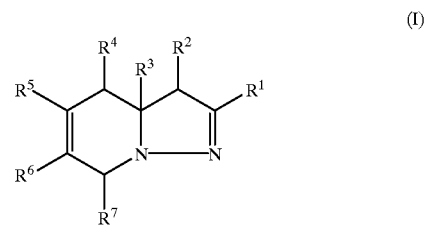

in which $R^1$ is a substituted or unsubstituted lower alkyl, lower alkenyl or lower alkynyl; $R^2$ is a hydroxy; $R^3$ is a lower alkoxycarbonyl; $R^4$ and $R^7$ are hydrogens or substituted or unsubstituted phenyl groups; $R^5$ and $R^6$ are hydrogens or lower alkyl groups; or pharmaceutically acceptable salts thereof, having cardioprotective activity. Also disclosed are methods of treating cardiovascular disease using a compound of formula (I) or pharmaceutically acceptable compositions comprising the compound of formula (I).

11 Claims, No Drawings

1,9-DIAZABICYCLO[4.3.0]NONA-3,8-DIENE DERIVATIVES

This application is a 371 of PCT/JP96/02192 filed Aug. 5, 1996.

TECHNICAL FIELD

The present invention relates to diazabicyclo compounds and pharmaceutically acceptable salts thereof and more particularly, to novel 1,9-diazabicyclo-[4.3.0]nona-3,8-diene derivatives and pharmaceutically acceptable salts thereof. Furthermore, the present invention relates to cardiovascular agents containing the diazabicyclo compounds or pharmaceutically acceptable salts thereof as an active ingredient.

INDUSTRIAL APPLICABILITY

The diazabicyclo compounds of the present invention are novel compounds having, as a basic skeleton, 1,9-diazabicyclo[4.3.0]nonan represented by the following formula (A):

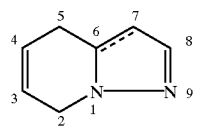
(A)

wherein the dotted line shows either double bond or single bond.

Accordingly, a first aspect of the present invention is to provide novel 1,9-diazabicyclo[4.3.0]-nona-3,8-diene compounds represented by the following formula (I):

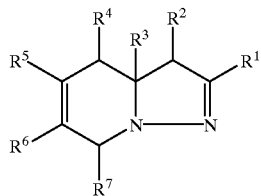
(I)

wherein $R^1$ is a group selected from the following:
(1) lower alkyl group or lower alkenyl group which may be substituted by cyano, nitro, lower alkylthio, lower alkylsulfinyl or lower alkylsulfonyl group,
(2) lower acyl group which may be substituted by heteroaryl group,
(3) heterocyclyl group which may be substituted by lower alkyl or lower alkoxycarbonyl group, and
(4) carbonyl group substituted by heteroaryl group, $R^2$ is a hydroxy group, $R^3$ is a lower alkoxycarbonyl group, $R^4$ and $R^7$, each of them being the same as the other, are hydrogen atoms or phenyl groups which may be substituted by halogen, cyano, lower alkyl, lower alkoxy, nitro, aryl or lower acyl group, and $R^5$ and $R^6$, each of them being the same as the other, are hydrogen atoms or lower alkyl groups, or pharmaceutically acceptable salts thereof.

Specifically, the present invention provides 1,9-diazabicyclo[4.3.0]nona-3,8-diene compounds represented by the following formula (I-a):

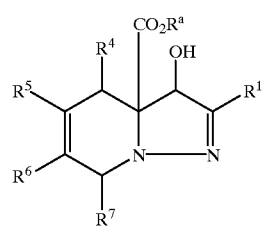
(I-a)

wherein
$R^a$ is a lower alkyl group, and
$R^1$, $R^4$, $R^5$, $R^6$ and $R^7$ have the same meanings as above,
or pharmaceutically acceptable salts thereof.

More specifically, the present invention provides 1,9-diazabicyclo[4.3.0]nona-3,8-diene compounds represented by the following formula (I-b):

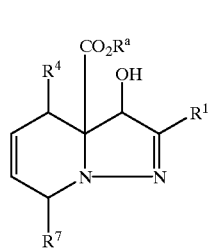
(I-b)

wherein $R^a$, $R^1$, $R^4$ and $R^7$ have the same meanings as above,
or pharmaceutically acceptable salts thereof.

Still more specifically, the present invention provides 1,9-diazabicyclo[4.3.0]nona-3,8-diene compounds represented by the following formula (I-c):

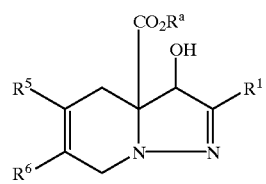
(I-c)

wherein $R^a$, $R^1$, $R^5$ and $R^6$ have the same meanings as above,
or pharmaceutically acceptable salts thereof.

A second aspect of the present invention is to provide cardiovascular agents comprising, as an active ingredient, said 1,9-diazabicyclo[4.3.0]nona-3,8-diene compounds or pharmaceutically acceptable salts thereof.

A third aspect of the present invention is to provide the use of said 1,9-diazabicyclo[4.3.0]-nona-3,8-diene compounds or pharmaceutically acceptable salts thereof as a medicament, or a method for the treatment of cardiovascular diseases in human being.

DETAILED DESCRIPTION OF THE INVENTION

It is to be understood that when the compounds of the present invention have one or more asymmetric carbon(s), those optically active compounds can be obtained by resolution of the diastereoisomeric mixture of these compounds by ordinary methods (see Examples mentioned later). Therefore, the optically active compounds and stereoisomeric mixture of the compounds should be included within the scope of the compounds of the present invention.

The compounds of the present invention may be converted to pharmaceutically acceptable acid addition salts thereof with an organic or inorganic acid. Examples of the organic acid include aliphatic acid such as formic acid, acetic acid, propionic acid, butyric acid, trifluoroacetic acid, trichloroacetic acid and the like; substituted or unsubstituted benzoic acid such as benzoic acid, p-nitrobenzoic acid and the like; lower-(halo)alkylsulfonic acid such as methanesulfonic acid, trifluoromethanesulfonic acid and the like; substituted or unsubstituted arylsulfonic acid such as benzenesulfonic acid, p-nitrobenzenesulfonic acid, p-bromobenzenesulfonic acid, toluenesulfonic acid, 2,4,6-triisopropylbenzenesulfonic acid and the like; and organic phosphoric acid such as diphenylphosphate. Examples of the inorganic acid include hydrochloric acid, sulfuric acid, hydrobromic acid, hydroiodic acid, borofluoric acid, perchloric acid, nitrous acid and the like.

Typical examples of the compounds of the present invention are as follows:

6,8-Diethoxycarbonyl-3,4-dimethylbicyclo[4.3.0]-1,9-diazanona-3,8-dien-7-ol (Compound No. 29);

6,8-Dimethoxycarbonyl-2,5-diphenyl-1,9-diazabicyclo[4.3.0]nona-3,8-dien-7-ol (Compound No. 31);

6,8-Diethoxycarbonyl-3(or 4)-methy-1,9-diazabicyclo[4.3.0]nona-3,8-dien-7-ol (Compound No. 35);

6,8-Dimethoxycarbonyl-3(or 4)-methybicyclo[4.3.0]-1,9-diazanona-3,8-dien-7-ol (Compound No. 36);

6,8-Dimethoxycarbonyl-2,5-bis(3-nitrophenyl)-7-hydroxy-1,9-diazabicyclo[4.3.0]nona-3,8-diene (Compound No. 48);

6,8-Dimethoxycarbonyl-2,5-di(4-cyano)phenyl-7-hydroxy-1,9-diazabicyclo[4.3.0]nona-3,8-diene (Compound No. 50);

2,5-Bis-(4-acetylphenyl)-6,8-dimethoxycarbonyl-7-hydroxy-1,9-diazabicyclo[4.3.0]nona-3,8-diene (Compound No. 51);

6,8-Dimethoxycarbonyl-2,5-di-p-tolyl-7-hydroxy-1,9-diazabicyclo[4.3.0]nona-3,8-diene (Compund No. 52);

6,8-Dimethoxycarbonyl-2,5-di(4-nitro)phenyl-7-hydroxy-1,9-diazabicyclo[4.3.0]nona-3,8-diene (Compound No. 53);

7-Amino-6,8-diethoxycarbonyl-3,4-dimethyl-1,9-diazabicyclo[4.3.0]nona-3,8-diene and HCl salt thereof (Compoud No. 81);

6,8-Diethoxycarbonyl-3,4-dimethyl-7-mercapto-1,9-diazabicyclo[4.3.0]nona-3,8-diene (Compound No. 82);

7-Amino-6,8-dimethoxycarbonyl-2,5-diphenyl-1,9-diazabicyclo[4.3.0]nona-3,8-diene and HCl salt thereof (Compoud No. 94);

3,4-Dimethyl-6-ethoxycarbonyl-7-hydroxy-8-hydroxymethy-1,9-diazabicyclo[4.3.0]nona-3,8-diene (Compound No. 104);

3,4-Dimethyl-6,8-dipropoxycarbonyl-7-hydroxy-1,9-diazabicyclo[4.3.0]nona-3,8-diene (Compound No. 124);

(−)-3,4-Dimethyl-6,8-dipropoxycarbonyl-7-hydroxy-1,9-diazabicyclo[4.3.0]nona-3,8-diene (Compound No. 126);

2,5-Diphenyl-8-guanidinocarbonyl-7-hydroxy-6-methoxycarbonyl-1,9-diazabicyclo[4.3.0]nona-3,8-diene (Compound No. 174);

2,5-Diphenyl-6-ethoxycarbonyl-7-hydroxy-8-propoxycarbonyl-1,9-diazabicyclo[4.3.0]nona-3,8-diene (Compound No. 139);

8-Cyano-3,4-dimethyl-7-hydroxy-6-propoxycarbonyl-1,9-diazabicyclo[4.3.0]nona-3,8-diene (Compound No. 164);

2,5-Diphenyl-7-hydroxy-6-methoxycarbonyl-8-(4-methylpiperazinyl)carbonyl-1,9-diazabicyclo[4.3.0]nona-3,8-diene and HCl salt thereof (Compound No. 168);

2,5-Diphenyl-7-hydroxy-6-methoxycarbonyl-8-(2-pyridyl)acetyl-1,9-diazabicyclo[4.3.0]nona-3,8-diene (Compound No. 171);

8-Diethylcarbamoyl-2,5-diphenyl-7-hydroxy-6-methoxycarbonyl-1,9-diazabicyclo[4.3.0]nona-3,8-diene (Compound No. 173);

8-((4S)-4,5-dihydro-4-methoxycarbonyl-2-oxazolyl)-2,5-diphenyl-7-hydroxy-6-methoxycarbonyl-1,9-diazabicyclo[4.3.0]nona-3,8-diene (Compound No.186);

8-(2,2-Dicyanoethenyl)-3,4-dimethyl-7-hydroxy-6-propoxycarbonyl-1,9-diazabicyclo[4.3.0]nona-3,8-diene (Compound No. 193);

3,4-Dimethyl-7-hydroxy-8-(1-hydroxy-2-nitroethyl)-6-propoxycarbonyl-1,9-diazaicyclo[4.3.0]nona-3,8-diene (Compound No. 199);

2,5-Diphenyl-7-hydroxy-6-methoxycarbonyl-8-methylsulfinylmethyl-1,9-diazabicyclo[4.3.0]nona-3,8-diene (Compound No. 205);

8-[(p-Carboxymethyl)phenoxy]methyl-2,5-diphenyl-7-hydroxy-6-methoxycarbonyl-1,9-diazabicyclo[4.3.0]nona-3,8-diene (Compound No. 209);

The compounds of the present invention have a cardioprotective effect on circulatory disturbance due to ischemia, anoxia or hypoxia. For example, the compounds of the present invention prevent the development of tissue damage which may occur because of the bloodstream obstruction in the brain, liver or heart due to cerebral infarction, myocardial infarction or angina pectoris, and accelerate the recovery of the cardiovascular function.

Useful drug therapy has not been established so far for circulatory disturbance due to ischemia, anoxia or hypoxia; however, the compounds of the present invention offer the possibility of a new, useful drug therapy in such a field.

Accordingly, a fourth aspect of the present invention is to provide cardiovascular agents containing the compounds of the formula (I) or pharmaceutically acceptable salts thereof, as an active ingredient.

In the specification of the present application, the term "lower" qualifying a group or a compound means that the group or the compound so qualified has 1 to 7, preferably 1 to 4, carbon atom(s).

The term "lower alkyl" referred to herein stands for a straight-chained or branched-chain alkyl and may include, for example, methyl, ethyl, n-propyl, isopropyl, n-butyl, isobutyl, sec-butyl, tert-butyl, n-pentyl, isopentyl, n-hexyl, isohexyl, n-heptyl, isoheptyl and the like. Among them, methyl, ethyl, n-propyl, isopropyl, n-butyl, isobutyl, sec-butyl, and tert-butyl is preferably used.

The term "lower alkenyl" stands for a straight-chained or branched-chain alkenyl and may include, for example, allyl, 2-methylallyl, ethenyl, 1-methylethenyl, 1-propenyl, 2-propenyl or 2-butenyl and the like.

"Lower alkynyl" may include, for example, propargyl, 2-methyl-propargyl, ethynyl and the like.

The term "lower alkoxy" stands for an lower alkyl-oxy group in which the "lower alkyl" group has the meaning mentioned above. Examples include methoxy, ethoxy, n-propoxy, isopropoxy, n-butoxy, isobutoxy, sec-butoxy, tert-butoxy, n-pentyloxy, isopentyloxy, n-hexyloxy, isohxyloxy, n-heptyloxy, isoheptyloxy and the like. Among them, methoxy, ethoxy, n-propoxy, isopropoxy, n-butoxy, iso-butoxy, sec-butoxy or tert-butoxy is preferably used.

The term "lower acyl" stands for a moiety obtainable by removing the hydroxy group from the carboxyl group of a lower aliphatic acid, and may include, for example, a lower alkanoyl group such as acetyl, propionyl, butyryl and the like.

"Lower alkoxycarbonyl" may include, for example, methoxycarbonyl, ethoxycarbonyl, propoxycarbonyl, isopropoxycarbonyl, butoxycarbonyl, sec-butoxycarbonyl, tert-butoxycarbonyl, pentyloxycarbonyl, hexyloxycarbonyl and the like.

The term "lower acyloxy" stands for a moiety obtainable by removing the hydrogen atom from the carboxyl group of a lower aliphatic acid, and may include, for example, acetoxy, propanoyloxy, butanoyloxy and the like.

The terms "lower alkylthio", "lower alkylsulfinyl" and "lower alkylsulfonyl" stand for the groups in which the respective "lower alkyl" groups have the same meaning as mentioned above.

"Halogen atom" may be chlorine, iodine, bromine or fluorine.

The term "aryl" stands for a monocyclic or polycyclic aryl group which may have at least one substituent(s) such as an alkyl group. Examples include phenyl, tolyl, xylyl, α-naphthyl, β-naphthyl and the like.

"Aryloxy" may include phenoxy, tolyloxy, xylyloxy, α-naphthyloxy, β-naphthyloxy and the like.

The term "heterocyclic" stands for a 3 to 8 membered, preferably 5 or 6 membered heterocyclic group containing at least one hetero atom(s) such as nitrogen, sulfur, and oxygen atom(s). Examples include a heterocyclic group containing 1 to 4 nitrogen atom(s), such as azetidinyl, pyrrolidinyl, imidazolyl, imidazolinyl, piperidinyl, pyrazolidinyl, piperazinyl and tetrahydropyrimidinyl; a heterocyclic group containing 1 to 2 oxygen atom(s) and 1 to 3 nitrogen atom(s), such as morpholynyl; and a heterocyclic group containing 1 to 3 sulfur atom(s) and 1 to 3 nitrogen atom(s), such as thiazolidinyl; and so on.

The term "heteroaryl" stands for a 5 or 6 membered aromatic cyclic group containing at least one hetero atom(s) such as nitrogen, sulfur, and oxygen atom(s). Examples include a group having 1 to 4 nitrogen atom(s), such as imidazolyl, pyridinyl and piperazil; a group having 1 to 2 oxygen atom(s) and 1 to 3 nitrogen atom(s), such as oxazolyl; and a group having 1 to 3 sulfur atom(s) and 1 to 3 nitrogen atom(s), such as thiazolyl and thiadiazolyl; and so on.

The compounds of the present invention of the formula (I) may be prepared in accordance with the processes as shown below.

Process 1:

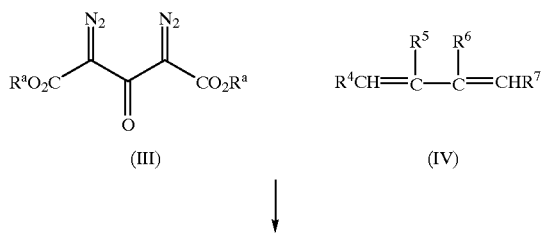

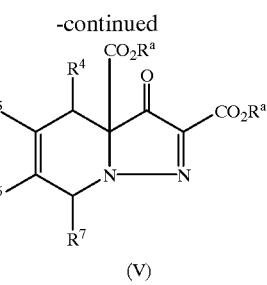

wherein $R^a$, $R^4$, $R^5$, $R^6$ and $R^7$ have the same meanings as above.

According to this Process 1, the diazabicyclo compound of the formula (V), corresponding to the compound of the present invention of the formula (I), in which the groups $R^1$ and $R^3$, each being the same as the other, are lower alkoxycarbonyl groups and the group $R^2$ is an oxo group, is prepared by Diels-Alder reaction of a 1,3-bis(diazo)-1,3-di-(lower)alkoxycarbonyl-2-propanone derivative of the formula (III) with a 1,3-butadiene derivative of the formula (IV).

The reaction of the compound of the formula (III) with the compound of the formula (IV) in an amount ranging from approximately 0.2 molar to approximately 5 molar may be carried out usually in an inert solvent, for example, an ether solvent, i.e., diethyl ether, tetrahydrofuran, dioxane or the like; a hydrocarbon solvent, i.e., benzene, toluene, xylene, cyclohexane or the like; a halogenated hydrocarbon solvent, i.e., dichloromethane, chloroform or the like; N,N-dimethylformamide, acetonitrile, dimethylsulfoxide, and so on.

Reaction temperature and reaction time are not limited to a particular range and may vary in a wide range according to the starting materials to be used. Preferably, the reaction may be carried out in a sealed vessel at the temperature of boiling point of the solvent to be used. The reaction may be finished in several hours to several days under these conditions. The compound of the formula (V) thus obtained has an endo-form, as is usually the case with compounds produced by Diels-Alder reaction. The obtained compound may be isolated and purified in conventional manner, such as by means of filtration, decantation, extraction, washing, removal of the solvent, column chromatography, thin-layer chromatography, recrystallization, distillation, sublimation and so on; however, the reaction mixture may be used for the next reaction without further purification.

The 1,3-Bis(diazo)-1,3-di-(lower)alkoxycarbonyl-2-propanone derivative of the formula (III) to be employed as a starting compound in the above Process 1 can be prepared by diazo reaction of a commercially available acetone-dicarboxylic acid di(lower)alkyl ester in accordance with the method described later in the examples.

Process 2:

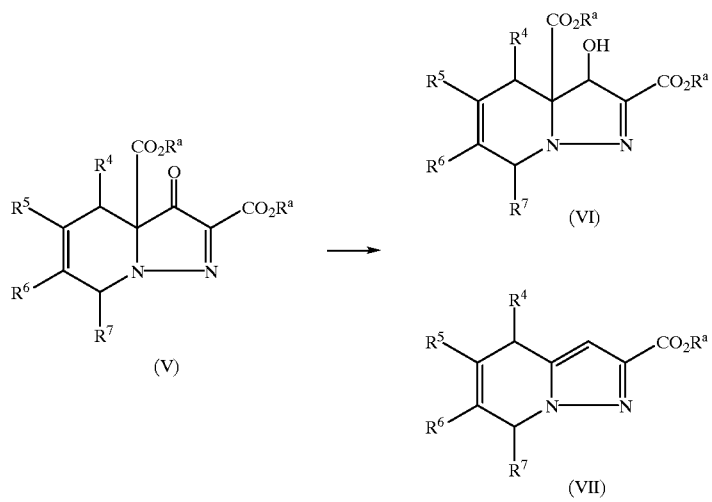

wherein $R^a$, $R^4$, $R^5$, $R^6$ and $R^7$ have the same meanings as above.

The diazabicyclo compound of the formula (VI), corresponding to the compound of the present invention of the formula (I), in which the groups $R^1$ and $R^3$, each being the same as the other, are lower alkoxycarbonyl groups and the group $R^2$ is a hydroxy group, is produced from the compound of the formula (V) obtained in Process 1 above by reductive reaction, that is, the reduction of the oxo group at 7-position to a hydroxy group. In this step, the compound of the formula (VII) can be produced as well, according to the reaction conditions employed.

The reaction can be carried out by using conventional method for reduction of carbonyl compounds to produce alcohols, for instance, using a reducing reagent in an amount ranging from 0.25 molar to 2 molar in such an inert solvent as enumerated above, under ice-cooling, and if neccessary, using cerium(III) chloride heptahydrate as a cataylst.

The reducing reagents employable in this process include, for example, lithium borohydride, sodium borohydride, lithium aluminum hydride and the like.

In this reduction process, the compound of the formula (VII) can be produced together with the compound of the formula (VI), when the reaction temperature is from room temperature to the temperature of the boiling point of the solvent.

The compounds of the formula (VI) and the compounds of formula (VII) thus obtained may be isolated and purified in conventional manner, such as by means of filtration, decantation, extraction, washing, removal of the solvent, column chromatography, thin-layer chromatography, recrystallization, distillation, sublimation and so on; however, the reaction mixture may be used for the next reaction without further purification.

The compounds of the formula (VI) obtained in this process have a hydroxy group at 7-position in the α- and β-configurations, and the α-configuration compound and the β-configuration compound are separable by ordinary method (see Example 4 mentioned later.). Therefore, each of the α-configuration and β-configuration compounds, and the stereoisomeric mixture of the compounds are all included in the compounds of the present invention.

The compounds of the formula (VI) obtained in this process show a good cardioprotective activity, and are also usable as a starting compound for making other diazabicyclo compounds of the present invention as mentioned below.

Process 3:

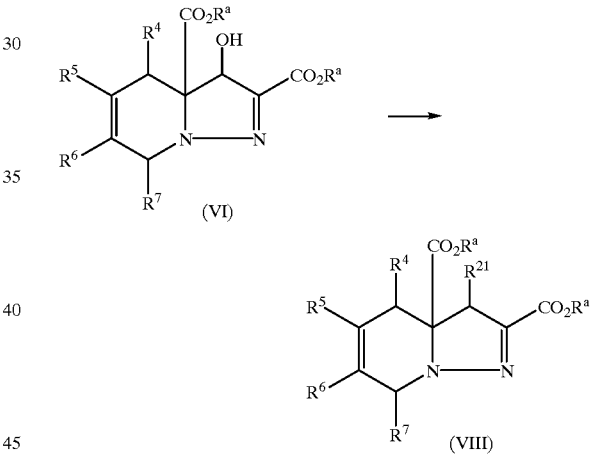

wherein $R^{21}$ is a mercapto, amino, mono- or di-(lower) alkylamino or lower acyloxy group, and $R^a$, $R^4$, $R^5$, $R^6$ and $R^7$ have the same meanings as above.

Process 3 is a step by which the diazabicyclo compound of the formula (VI) obtained in Process 2 above may be converted to produce the compound of the formula (VIII), corresponding to the compound of the present invention of the formula (I), in which the groups $R^1$ and $R^3$, each being the same as the other, are lower alkoxycarbonyl groups and the group $R^{21}$ is a mercapto, amino, mono- or di-(lower) alkylamino or lower acyloxy group, by the following reaction.

(1): $R^{21}$=mercapto group:

The compound of the formula (VIII), in which $R^{21}$ is a mercapto, is obtainable by the following:

First, the compound of the formula (VI) is reacted with an activated-reagent for a hydroxy group such as mesyl chloride in such an inert solvent as enumerated above and in the presence of a base to give the intermediate compound in which the hydroxy group at 7-position is substituted by an activated group such as mesyl group. Then, this intermediate is reacted with potassium thioacetate to produce the corresponding thioester derivative, and finally to conduct the hydrolysis of this thioester to give the compound of the formula (VIII), in which $R^{21}$ is a mercapto group.

The base to be used in the above reaction may be an oraganic base or an inorganic base, for example, alkali metal such as lithium, sodium, potassium and the like; alkaline earth metal such as calcium and the like; alkali metal hydride such as sodium hydride and the like; alkaline earth metal hydride such as calcium hydride and the like; alkali metal hydroxide such as sodium hydroxide, potassium hydroxide and the like; alkali metal carbonate such as sodium carbonate, potassium carbonate and the like; alkali metal bicarbonate such as sodium bicarbonate, potassium bicarbonate and the like; alkali metal alkoxide such as sodium methoxide, sodium ethoxide, potassium tert-butoxide and the like; alkali metal alkanoyl such as sodum acetate and the like; alkaline earth metal carbonate such as magnesium carbonate, calcium carbonate and the like; tri-(lower) alkylamine such as trimethylamine, triethylamine, N,N-di-isopropyl-N-ethylamine and the like; pyridine derivatives such as pyridine, picoline, lutidine, N,N-di-(lower) alkylaminopyridine (e.g. N,N-dimethylpyridine) and the like; quinoline; N-(lower)alkylmorpholine (e.g. N-methylmorpholine); N,N-di-(lower)alkylbenzylamine (e.g., N,N-dimethylbenzylamine); and so on.

(2): $R^{21}$=amino or mono- or di-(lower)alkylamino group:

The compound of the formula (VIII), in which $R^{21}$ is an amino or mono- or di-(lower)alkylamino, is obtainable by reaction of the intermediate compound in which the hydroxy group at 7-position is substituted by an activated group such as mesyl group mentioned above, with ammonia or mono- or di-(lower)alkylamine in such an inert solvent as enumerated above.

(3): $R^{21}$=lower acyloxy group:

The compound of the formula (VIII), in which $R^{21}$ is a lower acyloxy, is obtainable by reaction of the compound of formula (VI) with acid anhydride or acid halide of a lower aliphatic acid in the presence of the base mentioned above and in such an inert solvent as enumerated above.

The compounds of the formula (VIII) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 4:

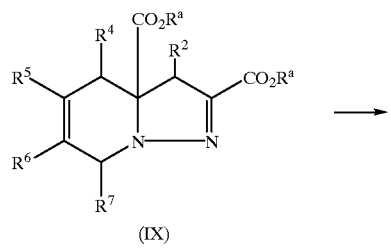

(IX)

-continued

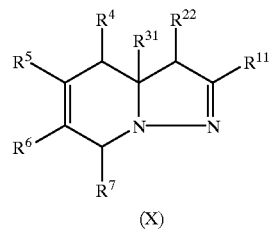

(X)

wherein $R^{11}$ and $R^{31}$ are hydroxymethyl, or when one of them is a lower alkoxycarbonyl group the other is a hydroxymethy group; $R^{22}$ is a hydroxy, mercapto, amino, mono- or di-(lower)alkylamino or lower acyloxy group; and $R^a$, $R^2$, $R^4$, $R^5$, $R^6$ and $R^7$ have the same meanings as above.

The diazabicyclo compound of the formula (X), corresponding to the compound of the present invention of the formula (I), in which $R^1$ and/or $R^3$ are/is hydroxymethyl group(s), is obtainable by reduction of the compound of the formula (IX).

The reaction of the compound of the formula (IX) with a reducing reagent such as lithium aluminum hydride, diisobutylaluminum hydride, lithium triethylborohydride or the like may be carried out in such an inert solvent as enumerated above.

The alkoxycarbonyl group at 8-position of the compound (IX) in which $R^4$ is hydrogen atom, can be preferentially converted to a hydroxymethyl group by reduction with lithium aluminum hydride or diisobutylaluminum hydride, and the alkoxycarbonyl group at 6-position of the compound (IX) in which $R^4$ is hydrogen atom, can be preferentially converted to a hydroxymethyl group by reduction with lithium triethylborohydride. Furthermore, the alkoxycarbonyl group at 8-position of the compound (IX) in which $R^4$ is other than hydrogen atom, can be preferentially converted to a hydroxymethyl group as compared with the alkoxycarbonyl group at 6-position.

By using this process, when $R^2$ of the compound (IX) is an oxo-group, the oxo-group can be converted to a hydroxy group.

When $R^2$ of the compound (IX) is a hydroxy, mercapto, amino or mono-(lower)alkylamino group, the group may be protected by a protecting group in conventional manner before the reducing reaction, to remove the protecting group after the reaction.

The compound of the formula (X) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 5:

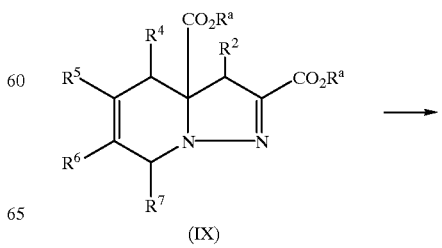

(IX)

-continued

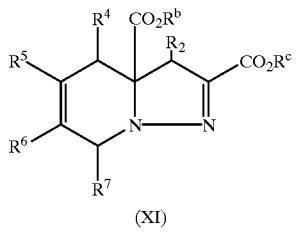

wherein $R^b$ and $R^c$ are hydrogen atoms or each of them being the same as or different from the other, are substituted or unsubstituted lower alkyl groups; and $R^a$, $R^2$, $R^4$, $R^5$, $R^6$ and $R^7$ have the same meanings as above.

Process 5 is a step to exchange the ester group(s) at 6- and/or 8-position(s) of the compound (IX) for other ester group(s), and to give the ester compound represented by the formula (XI).

The compound of the formula (XI) in which $R^b$ and/or $R^c$ are(is) hydrogen atom(s) is obtainable by hydrolysis of the compound of the formula (IX) with an acid or a base. Then, this carboxylic acid compound is treated with lower aliphatic alcohol in the presence of a coupling agent such as dicyclohexylcarbodiimide, or is converted to an acid chloride derivative by reaction with thionyl chloride and then treated with lower aliphatic alcohol in the presence of a base, to give the compound of the formula (XI).

In this process, when the group $R^4$ of the compound (IX) is a bulky group such as phenyl, the carboxy group at 8-position can be preferentially reacted. Thus, the process provides the compound of the formula (XI), in which $R^b$ and $R^c$, each being the same as or different from the other, are substituted or unsubstituted lower alkyl groups.

When the group $R^2$ of the starting compound (IX) is a hydroxy, mercapto, amino or mono-(lower)alkylamino group, the group may be protected by a protecting group in conventional manner before the reaction, to remove the protecting group after the reaction.

The lower aliphatic alcohol to be used in this process may be, for example, methanol, ethanol, n-propanol, isopropanol, n-butanol, iso-butanol, tert-butanol and the like, and the alcohol may be substituted by nitro, amino, mono- or di-(lower)alkylamino such as ethylamino, diethylamino and the like; lower alkoxycarbonyl such as methoxycarbonyl, ethoxycarbonyl and the like; aryl such as phenyl, α-naphthyl and the like; heterocyclyl such as azetidinyl, pyrrolidinyl, imidazolyl, imidazolidinyl, piperidinyl, pyrazolidinyl, piperazinyl, tetrahydropyrimidinyl, morpholinyl, thiazolidinyl and the like; heteroaryl such as imidazolyl, pyridinyl, piperazyl, oxazolyl, thiazolyl, thiadiazolyl and the like.

The compound of the formula (XI) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

The compound of the formula (XII), corresponding to the compound of the present invention of the formula (I), in which the group $R^1$ is hydrogen atom, $R^2$ is an oxo and $R^3$ is an ester-exchanged lower alkoxycarbonyl group, is obtainable by reaction of the compound of the formula (V), corresponding to the starting compound (IX), in which 7-position is an oxo-group, with a substituted or unsubstituted lower aliphatic alcohol in the presence of a catalyst, e.g., titanium(IV) isopropoxide, under heating at the temperature of the boiling point of the solvent, as indicated in the reaction scheme below.

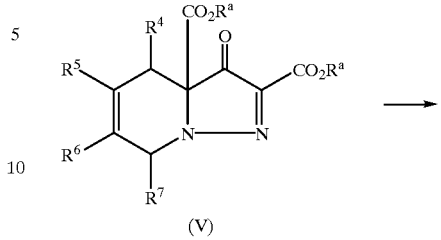

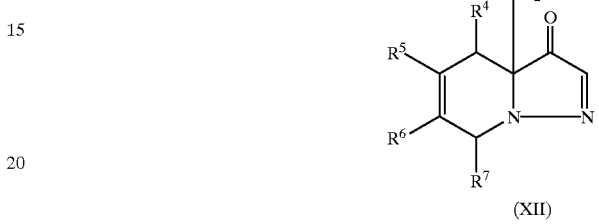

wherein $R^a$, $R^b$, $R^4$, $R^5$, $R^6$ and $R^7$ have the same meanings as above.

The compound of the formula (XII) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 6:

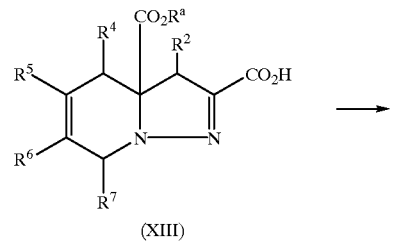

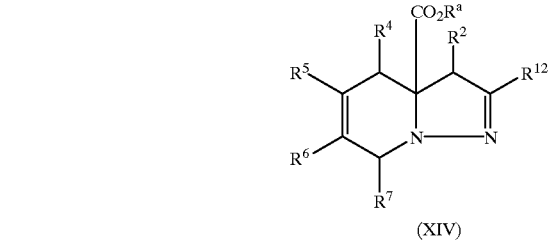

wherein $R^{12}$ is a carbonyl or thiocarbonyl group substituted by amino, mono- or di-(lower)alkylamino, guanidino, aryl, heterocyclyl or hetroaryl; a cyano group; or a substituted or unsubstituted lower acyl group; and $R^a$, $R^2$, $R^4$, $R^5$, $R^6$ and $R^7$ have the same meanings as above.

Process 6 is a step by which the diazabicyclo compound of the formula (XIV), corresponding to the compound of the present invention of the formula (I), in which the group $R^1$ is selected from the various groups mentioned above, is prepared from the compound of the formula (XIII) having a carboxy group at 8-position obtained in Process 5, according to the following manner.

(1): $R^{12}$=carbonyl group substituted by amino, mono- or di-(lower)alkylamino, guanidino or heterocyclyl group:

The compound of the formula (XIV), in whcih $R^{12}$ is a carbonyl group substituted by an amino, mono- or di-(lower) alkylamino, guanidino or heterocyclyl group, is obtainable by subjecting the compound of the formula (XIII) to an amido formation reaction of the carboxyl group activated in advance, in conventional manner.

For example, the compound (XIII) is converted to an acid chloride by reaction with thionyl chloride in such an appropriate inert solvent as enumerated in Process 1, and, this acid chloride is treated with corresponding amine in the presence of an appropriate base to give the compound of the formula (XIV).

The compound of the formula (XIV) is also obtainable by reacting the compound (XIII) with amine in the presence of a dehydration reagent such as dicyclohexylcarbodiimide.

Suitable amine may include ammonia, diethylamine, guanidine, N-methylpiperidine, morpholine, N-methylpiperazine, and the like.

(2): $R^{12}$=carbonyl group substituted by aryl or heteroaryl group:

The compound of the formula (XIV), in which the group $R^{12}$ is a carbonyl group substituted by aryl or heteroaryl group, is obtainable by reacting the acid chloride derivative of the compound of the formula (XIII) with a halogenated aryl or heteroaryl compound in the presence of a base such as n-butyllithium.

Suitable halogenated aryl or heteroaryl compound may include chlorobenzene, bromobenzene, 2-bromobenzene and 2-bromopyridine, which may be substituted by other group(s).

(3): $R^{12}$=thiocarbonyl group substituted by amino, mono- or di-(lower)alkylamino, guanidino, aryl, heterocyclyl or heteroaryl group:

The compound of the formula (XIV), in which $R^{12}$ is a thiocarbonyl group substituted by amino, mono- or di-(lower)alkylamino, guanidino, aryl, heterocyclyl or heteroaryl group, is obtainable by reacting the compound of the formula (XIV), in which $R^{12}$ is a carbonyl group substituted by the group mentioned above, with Lawesson's Reagent [(MeO—$C_6H_4$P(=S)S)$_2$].

(4): $R^{12}$=cyano group:

The compound of the formula (XIV), in which $R^{12}$ is a cyano group, is obtainable by reacting the compound of the formula (XIV), in which $R^{12}$ is a carbamoyl group obtained in Process 6-(1), with a dehydration reagent such as thionyl chloride or phosphorus oxychloride in the presence of an appropriate base.

(5): $R^{12}$=substituted or unsubstituted lower acyl group:

The compound of the formula (XIV), in which $R^{12}$ is a substituted or unsubstituted lower acyl, is obtainable by reacting the compound of the formula (XIII), in which the carboxyl group is activated by the method described in Japanese Patent Kokai No. 59-144794, with Grignard reagent or lithium reagent which may be substituted by various groups.

Suitable Grignard reagent may include iodinated lower alkylmagnesium, and lithium reagent may include lower alkyllithium. The lower alkyl groups of these reagents may be substituted by nitro, amino, mono- or di-(lower) alkylamino, lower alkoxycarbonyl, aryl such as phenyl, tolyl, xylyl, α-naphthyl, β-naphthyl and the like; heterocyclyl such as azetidinyl, pyrrolidinyl, imidazolynyl, imidazolidinyl, piperidinyl, pyrazolidinyl, piperazinyl, tetrahydropyrimidinyl, morpholinyl, thiazolidinyl and the like; or heteroaryl such as imidazolyl, pyridyl, piperazyl, oxazolyl, thiazolyl, thiadiazolyl and the like.

Furthermore, the compound of the formula (XIV), in which $R^{12}$ is a nitro-substituted lower acyl, is also obtainable by reacting the compound of the formula (XIII), in which the carboxyl group at 8-position is activated in advance by a carboxylic acid activating reagent such as carbonyldiimidazole, with a nitro-substituted lower alkane in the presence of an appropriate base such as sodium hydride.

When the group $R^2$ of the starting compound (XIII) is a hydroxy, mercapto or amino group, the group may be protected by a protecting group in conventional manner before the reaction, to remove the protecting group after the reaction.

The compound of the formula (XIV) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 7:

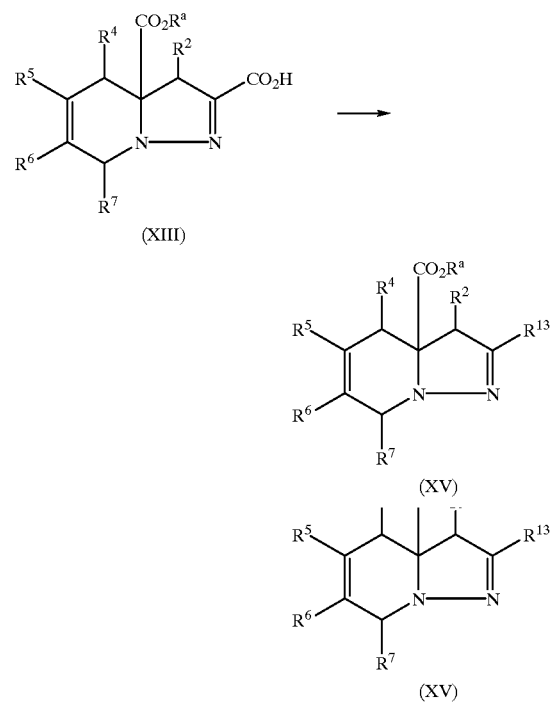

wherein $R^{13}$ is a heterocyclyl or heteroaryl group which may be substituted by a lower alkyl or lower alkoxycarbonyl group; and $R^a$, $R^2$, $R^4$, $R^5$, $R^6$ and $R^7$ have the same meanings as above.

Process 7 is a step by which the diazabicyclo compound of the formula (XV), corresponding to the compound of the present invention of the formula (I), in which the group $R^1$ is selected from the various groups mentioned above, is prepared from the compound of the formula (XIII) having a carboxyl group at 8-position, according to the following manner.

(1): $R^{13}$=1,3-oxazolin-2-yl group:

The compound of the formula (XV), in which $R^{13}$ is 1,3-oxazolin-2-yl, is obtainable by reacting the compound of the formula (XIII) with hydroxyethylamine, triphenylphosphine and carbon tetrachloride in the presence of an appropriate base such as triethylamine.

(2): $R^{13}$=1,2,4-triazol-3-yl group:

The compound of the formula (XV), in which $R^{13}$ is 1,2,4-triazol-3-yl, is obtainable by reacting the compound of the formula (XIII) with N-di-methoxymethyl-N,N-dimethylamine, and then by treating the resulting compound with hydrazine.

(3): $R^{13}$=4-methoxycarbonyl-1,3-oxazolin-2-yl or 4,4-dimethyl-1,3-oxazolin-2-yl group:

The compound of the formula (XV), in which $R^{13}$ is 4-methoxycarbonyl-1,3-oxazolin-2-yl or 4,4-dimethyl-1,3-oxzolin-2-yl, is obtainable by reacting the compound of the formula (XIII), in which the carboxyl group is activated in advance in the same manner as described in Process 6-(1), with serine methyl ester or 2,2-dimethylaminoethanol, and then by treating the resulting compound with thionyl chloride.

(4): $R^{13}$=1,2,4-oxadiazol-3-yl group:

The compound of the formula (XIV) having a cyano group at 8-position is obtained in accordance with Process 6-(4), then, this compound is treated with hydroxylamine in the presence of an alkali and further treated with boron trifluoride etherate and ethyl orthoformate to give the compound of the formula (XV) in which $R^{13}$ is 1,2,4-oxadiazol-3-yl group.

(5): $R^{13}$=1,3-imidazolin-2-yl group:

The compound of the formula (XV), in which $R^{13}$ is 1,3-imidazolin-2-yl, is obtainable by reacting the thiocarbamoyl compound of the formula (XIV), obtained in Process 6-(3), with ethylenediamine.

(6): $R^{13}$=1,2,4-thiadiazol-5-yl group:

The compound of the formula (XV), in which $R^{13}$ is 1,2,4-thiadiazol-5-yl, is obtainable by reacting the thiocarbamoyl compound of the formula (XIV) obtained in Process 6-(3), with N-dimethoxymethyl-N,N-dimethylamine, and by treating the resulting compound with o-(mesitylenesulfonyl) hydroxylamine.

(7): $R^{13}$=1,3-thiazolin-2-yl group:

The compound of the formula (XV), in which $R^{13}$ is 1,3-thiazolin-2-yl, is obtainable by reacting the thiocarbamoyl compound of the formula (XIV) obtained in Process 6-(3), with methyl iodide, and by treating the resulting compound with cysteamine hydrochloride in the presence of an appropriate base.

(8): $R^{13}$=4-ethoxycarbonyl-1,3-thiazol-2-yl group:

The compound of the formula (XV), in which $R^{13}$ is 4-ethoxycarbonyl-1,3-thiazol-2-yl, is obtainable by reacting the thiocarbamoyl compound of the formula (XIV) obtained in Process 6-(3), with ethyl bromopyruvate.

(9): $R^{13}$=1,3-imidazol-2-yl group:

The compound of the formula (XV), in which $R^{13}$ is 1,3-imidazol-2-yl, is obtainable by reacting the thiocarbamoyl compound of the formula (XIV) obtained in Process 6-(3), with methyl iodide, then, by reacting the resulting compound with aminoacetaldehyde dimethyl acetal, and further treating with an acid.

When the group $R^2$ of the starting compound (XIII) is a hydroxy, mercapto or amino group, the group may be protected by a protecting group in conventional manner before the reaction, to remove the protecting group after the reaction.

The compound of the formula (XV) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 8:

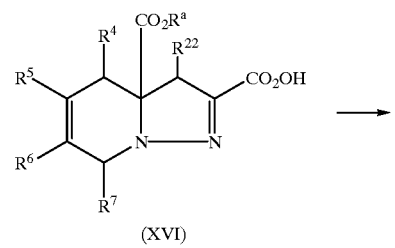

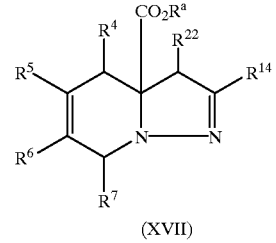

wherein $R^{14}$ is a lower alkyl, lower alkenyl or lower alkynyl group which may be substituted by cyano, nitro, amino, mono- or di-(lower)alkylamino, lower acyloxy, hydroxy, lower alkoxy, aryloxy, lower alkoxycarbonyl, lower alkylthio, lower alkylsulfinyl, lower alkylsulfonyl, aryl, heterocyclyl or heteroaryl; and $R^a$, $R^{22}$, $R^4$, $R^5$, $R^6$ and $R^7$ have the same meanings as above.

The Process 8 is a step by which the diazabicyclo compound of the formula (XVII), corresponding to the compound of the present invention of the formula (I), in which the group $R^1$ is selected from the various groups mentioned above, is prepared from the compound of the formula (XVI) having an alkoxycarbonyl group at 6-position and a hydroxymethyl group at 8-position obtained in Process 4, according to the following manner.

(1): $R^{14}$=lower alkyl group substituted by amino or mono- or di-(lower)alkylamino group:

The compound of the formula (XVI) having a hydroxymethyl group at 8-position is treated with mesyl chloride to activate said hydroxymethyl group, and then treated with ammonia or mono- or di-(lower)alkylamine to give the compound of the formula (XVII), in which $R^{14}$ is a lower alkyl group substituted by amino or mono- or di-(lower) alkylamino group.

(2): $R^{14}$=lower alkyl group substituted by lower alkylthio, lower alkylsulfinyl or lower alkylsulfonyl group:

The compound of the formula (XVI) is treated with a lower alkyl substituted disulfide such as dimethyl disulfide in the presence of a reducing reagent such as tributylphosphine to give the compound of the formula (XVII) in which $R^{14}$ is a lower alkylthio-substituted lower alkyl group. Then, treating the compound obtained above with hydrogen peroxide gives the compound of the formula (XVII) in which $R^{14}$ is a lower alkylsulfinyl or lower alkylsulfonyl group.

(3): $R^{14}$=lower alkyl, lower alkenyl or lower alkynyl group which may be substituted by hydroxy, nitro, aryl, lower alkoxycarbonyl or cyano group:

The hydroxymethyl group at 8-position of the compound of the formula (XVI) is converted to formyl group by subjecting the compound (XVI) to an oxidation reaction using a conventional oxidatin reagent such as manganese (IV) oxide, chromic acid or DMSO, or n-$Pr_4NRuO_4$ with N-methylmorpholine N-oxide. The obtained compound of the formula (XVI) having a formyl group at 8-position (i.e., intermediate compound) is treated with a nitroalkane compound such as nitromethane in the presence of Lewis acid to give the compound of the formula (XVII) in which $R^{14}$ is a hydroxy- and nitro-substituted lower alkyl group. Then, this compound is subjected to dehydration reaction with a dehydration reagent such as dicyclohexylcarbodiimide (DCC) to give the compound of the formula (XVII) in which $R^{14}$ is a nitro-substituted lower alkenyl group.

The above-obtained compound (XVII) may be converted to the compound (XVII) in which $R^{14}$ is a nitro-substituted lower alkyl group by treatment with sodium borohydride.

The compound of the formula (XVII) in which $R^{14}$ is a di-cyano-substituted lower alkenyl, is obtainable by reacting the intermediate compound (XVI) having a formyl group at 8-position, with malononitrile. This compound can be converted to the compound (XVII) in which $R^{14}$ is a di-cyano and nitro-substituted lower alkyl group, by treatment with nitromethane in the presence of 1,8-diazabicyclo[5.4.0]undec-7-ene (DBU).

The compound of the formula (XVII) in which $R^{14}$ is an alkenyl group substituted by the various groups mentioned above is obtainable by Wittig reaction of the intermediate compound (XVI) having a formyl group at 8-position.

(4): $R^{14}$=lower alkenyl group substituted by lower alkylsulfonyl group:

The compound of the formula (XVII) in which $R^{14}$ is a lower alkenyl group substituted by lower alkylsulfonyl is obtainable by reacting the intermediate compound (XVI) having a formyl group at 8-position, with Wittig reagent such as $(EtO)_2P(O)CH_2SO_2CH_3$ in the presence of an appropriate base such as sodium methoxide.

(5): $R^{14}$=lower alkyl group substituted by heterocyclyl group:

The compound of the formula (XVII) in which $R^{14}$ is a lower alkyl group substituted by heterocyclyl group is obtainable by subjecting the intermediate compound (XVI) having a formyl group at 8-position obtained in Process 8-(3), to reductive amination reaction such as treatment with heterocyclyl derivatives, for example, azetidine, piperidine, piperazine or N-(lower)alkyl piperazine in the presence of sodium cyanoborohydride.

(6): $R^{14}$=lower alkyl group substituted by lower acyloxy group:

The compound of the formula (XVII) in which $R^{14}$ is a lower alkyl group substituted by lower acyloxy group is obtainable by reacting the compound of the formula (XVI) with an acid anhydride of lower aliphatic carboxylic acid in the presence of an appropriate base.

(7): $R^{14}$=lower alkyl group substituted by aryloxy group:

The compound of the formula (XVII) in which $R^{14}$ is a lower alkyl group substituted by aryloxy group is obtainable by reacting the compound of the formula (XVI) with a substituted or unsubstituted arylalcohol in the presence of triphenylphosphine and di-(lower)alkyl azodicarboxylate in such an inert solvent as enumerated in Process 1.

When the group $R^{22}$ of the starting compound (XVI) is a hydroxy, mercapto or amino group, the group may be protected by a protecting group in conventional manner before the reaction, to remove the protecting group after the reaction.

The compound of the formula (XVII) thus obtained may be isolated and purified in conventional manner, such as by means of filtration, decantation, extraction, washing, removal of the solvent, column chromatography, thin-layer chromatography, recrystallization, distillation, sublimation, and so on; however, the reaction mixture may be used for the next reaction without further purification.

Process 9: (Other Compounds):

(1): The compound of the formula (I) in which $R^1$ is a carboxyl group, $R^2$ is hydrogen atom, $R^3$ is null, and a double bond exists between 6- and 7-positions:

This compound is obtainable from the compound of the formula (VI) by reaction with sodium hydroxide in an alcoholic solvent.

(2): The compound of the formula (I) in which $R^1$ and $R^3$ are carbamoyl groups and $R^2$ is a hydroxy group:

This compound is obtainable from the compound of the formula (VI) by reaction with ammonia in an alcoholic solvent.

When the group at 7-position of the starting compound is a hydroxy, mercapto or amino group, the group may be protected by a protecting group in conventional manner before the reaction, to remove the protecting group after the reaction.

These compounds obtained may be isolated and purified in conventional manner, such as by means of filtration, decantation, extraction, washing, removal of the solvent, column chromatography, thin-layer chromatography, recrystallization, distillation, sublimation, and so on.

The compounds of the present invention represented by the formula (I) thus produced may be converted to pharmaceutically acceptable acid addition salts thereof with organic or inorganic acids. Examples of the organic acid include aliphatic acid such as formic acid, acetic acid, propionic acid, butyric acid, trifluoroacetic acid, trichloroacetic acid and the like; unsubstituted or substituted benzoic acid such as benzoic acid, p-nitrobenzoic acid and the like; lower-(halo)alkylsulfonic acid such as methanesulfonic acid, trifluoromethanesulfonic acid and the like; substituted or unsubstituted arylsulfonic acid such as benzenesulfonic acid, p-nitrobenzenesulfonic acid, p-bromobenzenesulfonic acid, toluenesulfonic acid, 2,4,6-tri-isopropylbenzenesulfonic acid and the like; organic phosphoric acid such as diphenylphosphoric acid. Examples of the inorganic acid include hydrochloric acid, sulfuric acid, hydrobromic acid, hydroiodic acid, borofluoric acid, perchloric acid, nitrous acid and the like.

The compounds of the formula (I) according to the present invention may be administered orally to human being in the form of a pharmaceutically acceptable composition containing an effective amount thereof. The dose to be administered may vary in a wide range according to the age, weight and condition of patients; however, it is preferable to administer oral doses of, for example, 10–1000 mg a day at one time or divided into 2–3 times.

The oral formulations of the cardiovascular agent according to the present invention may include tablets, capsules, pulveres, troches or liquid preparations. These formulations may be formed by procedures known per se to those skilled in the art in the field of pharmaceutical formulations. For instance, the compound of the present invention of the formula (I) is suitably mixed with an excipient such as starch, mannitol, lactose and so on; a binder such as sodium carboxymethylcellulose, hydroxypropylmethylcellulose and so on; a disintegrators such as crystalline cellulose, calcium carboxymethylcellulose and so on; a lubricant such as talc, magnesium stearate and so on; a fluidity improvement agent such as light anhydrous silicic acid, to obtain preparations of tablets, capsules, pulveres, granules or troches.

The compound of the formula (I) according to the present invention may also be administered in the form of injectable formulations. Such formulations may include, for example, injectable solutions by dissolving or dispersing the compound in physiological saline with a conventional surfactant or dispersing agent; and crystalline or lyophilizing powder formurations for injection. The formulations may contain conventional pH-adjusting agents or stabilizers.

The dose range and administration route of the injectable formulations are not citical and may vary in a wide range with the age, weight, and condition of patients; however, the injectable formulations may be administered via intravenous, intra-arterial, subcutaneous or intraperitoneal route by injection at once or by drip-feed way.

The following Preparations and Examples are given for the purpose of illustrating this invention in more datail.

In the description below, the following symbols are used to have the particular meanings.

Me: methyl group
Et: ethyl group
Pr: propyl group
Bu: butyl group
Hex: hexyl group
Ac: acetyl group
Ph: phenyl group
Py: pyridyl group Preparation 1:

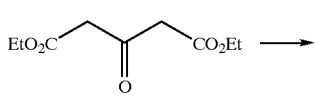

To a solution of 28.6 g (141 mmol) of diethyl 1,3-acetonedicarboxylate and 101.9 g (290 mmol) of p-dodecylbenzenesulfonazide in 90 ml of acetonitrile was added 40.4 ml (290 mmol) of triethylamine under ice-cooling, and the reaction mixture was stirred for 2 hours at room temperature. After removal of the solvent under reduced pressure, the resulting residue was purified by silica gel column chromatography (n-hexane—ethyl acetate) to give 35.9 g (quantitative) of Compound (1) as pale yellowish oil.

$^1$H-NMR (CDCl$_3$) δ: 1.31 (t, 3H, J=6.9 Hz), 1.31 (t, 3H, J=6.9 Hz), 4.28 (q, 2H, J=6.9 Hz), 4.28 (q, 2H, J=6.9 Hz).

Preparation 2:

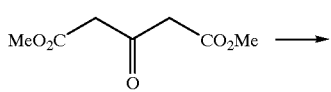

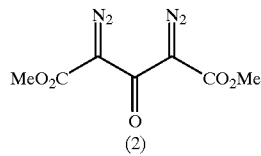

Compound (2) was obtained in substantially the same manner as that of Preparation 1.

$^1$H-NMR (CDCl$_3$) δ: 3.83 (s, 3H), 3.83 (s, 3H).

EXAMPLE 1

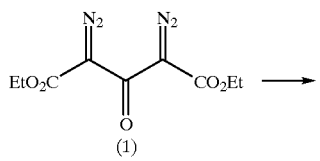

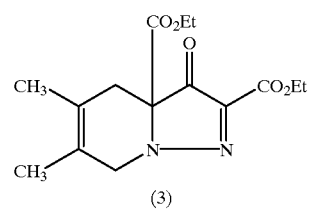

A mixture solution of 6.18 g (24.3 mmol) of Compound (1) obtained in Preparation 1 and 10 g (121.7 mmol) of 2,3-dimethyl-1,3-butadiene in 4 ml of tetrahydrofuran was heated and stirred in a sealed vessel at 80° C. for 12 days. After the reaction solvent was removed under reduced pressure, the resulting residue was purified by silica gel column chromatography (n-hexane-ethyl acetate) to give 4.26 g (56.9%) of Compound (3) as yellowish crystals.

$^1$H-NMR (CDCl$_3$) δ: 1.25 (t, 3H, J=6.9 Hz), 1.38 (t, 3H, J=6.9 Hz), 1.70 (s, 3H), 1.74 (s,3H), 2.35 (d, 1H, J=16.8 Hz), 3.08 (d, 1H, J=16.8 Hz), 4.16–4.28 (m, 2H), 4.34–4.42 (m, 4H).

EXAMPLE 2

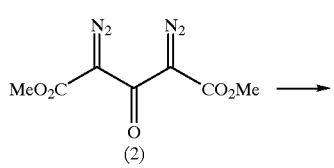

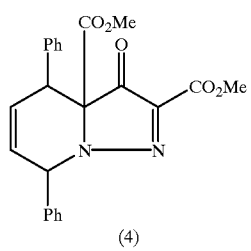

A mixture solution of 0.5 g (2.2 mmol) of Compound (2) obtained in Preparation 2 and 2.23 g (10.8 mmol) of 1,4-diphenyl-1,3-butadiene in 4 ml of tetrahydrofuran was heated and stirred in a sealed vessel at 80° C. for 6 days. After the reaction solvent was removed under reduced pressure, the resulting residue was purified by silica gel column chromatography (n-hexane-ethyl acetate) to give 357 mg (39.9%) of Compound (4) as colorless crystals.

$^1$H-NMR (CDCl$_3$) δ: 3.67 (s, 3H), 3.88 (s, 3H), 4.86 (d, 1H, J=5.6 Hz), 5.72 (d, 1H, J=2.0 Hz), 6.01–6.05 (m, 1H), 6.14–6.20 (m, 1H), 7.20–7.29 (m, 5H), 7.44–7.51 (m, 5H).

EXAMPLE 3

The compounds of the formula (V) listed in Table 1 were obtained in substantially the same manners as those described in Process 1, Example 1 and Example 2 above.

The following is physiochemical data of the representative compound listed in Table 1.

Compound (15):

$^1$H-NMR (CDCl$_3$) δ: 1.25 (t, 3H, J=6.9 Hz), 1.38 (t, 3H, J=6.9 Hz), 2.39–2.49 (m, 1H), 3.31 (dd, 1H, J=5.9 & 17.2 Hz), 3.55 (s, 3H), 4.12–4.42 (m, 4H), 5.68–5.69 (m, 1H), 5.72–5.83 (m, 1H), 6.17–6.24 (m, 1H).

TABLE 1

(V)

| Compound No. | R$^a$ | R$^4$ | R$^7$ | R$^5$ | R$^6$ |
|---|---|---|---|---|---|
| 5 | t-Bu | H | H | Me | Me |
| 6 | n-Hex | H | H | Me | Me |
| 7 | Me | H | H | Me | Me |
| 8 | Et | H | H | | Me |
| 9 | Me | H | H | | Me |
| 10 | Et | —CH$_2$CH$_2$— | | H | H |
| 11 | Me | H | H | H | H |
| 12 | Me | 3-Py | H | H | H |
| 13 | Me | 3-Py | 3-Py | H | H |
| 14 | Me | Me | Me | H | H |
| 15 | Et | H | OMe | H | H |
| 16 | Me | n-Hex | n-Hex | H | H |
| 17 | Et | OAc | H | H | H |
| 18 | Et | OMe | H | H | H |
| 19 | t-Bu | Ph | Ph | H | H |
| 20 | Et | Ph | Ph | H | H |
| 21 | Me | Ph-m-NO$_2$ | Ph-m-NO$_2$ | H | H |
| 22 | Me | Ph-p-Cl | Ph-p-Cl | H | H |
| 23 | Me | Ph-p-CN | Ph-p-CN | H | H |
| 24 | Me | Ph-p-COMe | Ph-p-COMe | H | H |
| 25 | Me | Ph-p-Me | Ph-p-Me | H | H |
| 26 | Me | Ph-p-NO$_2$ | Ph-p-NO$_2$ | H | H |
| 27 | Me | Ph-p-OMe | Ph-p-OMe | H | H |
| 28 | Me | Ph-p-Ph | Ph-p-Ph | H | H |

EXAMPLE 4

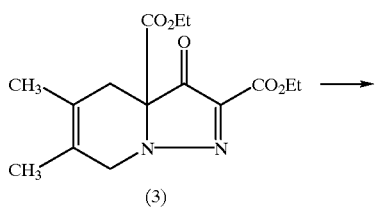
(3)

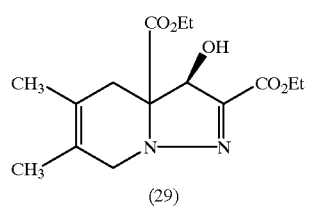
(29)

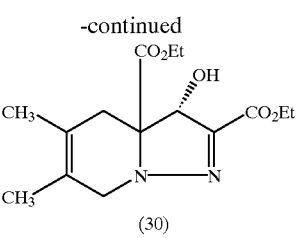
(30)

To a mixture solution of 301 mg (13.8 mmol) of lithium borohydride in 60 ml of tetrahydrofuran was added dropwise a solution of 4.26 g (13.8 mmol) of Compound (3) obtained in Example 1 in 200 ml of tetrahydrofuran under N$_2$ gas atmosphere at 0° C. After the dropwise, the reaction mixture was stirred at room temperature for 1 hour. Then, 28 ml of water was added to the reaction mixture and the solvent was removed under reduced pressure. The resulting residue was dissolved in ethyl acetate and the organic layer was washed with 1N-HCl solution, 5%-sodium bicarbonate aqueous solution and saturated saline, and dried over magnesium sulfate. The solvent was removed under reduced pressure and the resulting residue was purified by silica gel column chromatography (chloroform-acetone) to give 2.525 g (58.9%) of Compound (29) as pale yellowish crystals and 0.569 g (13.3%) of Compound (30) as pale yellowish oil.

Compound (29):

$^1$H-NMR (CDCl$_3$) δ: 1.24 (t, 3H, J=6.9 Hz), 1.35 (t, 3H, J=6.9 Hz), 1.63 (s, 3H), 1.70 (s, 3H), 2.44 (d, 1H, J=16.8 Hz), 2.85 (d, 1H, J=16.8 Hz), 3.07 (brs, 1H), 4.06–4.24 (m, 4H), 4.32 (q, 2H, J=6.9 Hz), 5.19 (s, 1H).

Compound (30):

$^1$H-NMR (CDCl$_3$) δ: 1.28 (t, 3H, J=6.9 Hz), 1.34 (t, 3H, J=6.9 Hz), 1.60 (s, 3H), 1.62 (s, 3H), 2.22 (d, 1H, J=16.5 Hz), 2.41 (d, 1H, J=16.5 Hz), 4.13 (s, 2H), 4.21–4.42 (m, 5H), 4.87 (s, 1H).

EXAMPLE 5

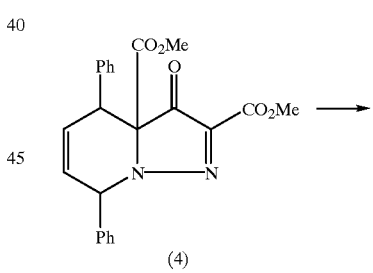
(4)

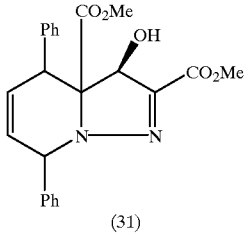
(31)

To a mixture solution of 19 mg (0.88 mmol) of lithium borohydride in 2 ml of tetrahydrofuran was added dropwise a solution of 0.357 g (0.88 mmol) of Compound (4) obtained in Example 2 in 4.5 ml of tetrahydrofuran under N$_2$ gas atmosphere at 0° C. After that, the reaction mixture was stirred at the same temperature for 1 hour. Then, saturated ammonium chloride aqueous solution was added to the reaction mixture and the solvent was extracted with ethyl acetate. The organic layer was washed with saturated saline and dried over magnesium sulfate. The solvent was removed under reduced pressure and the resulting residue was purified by silica gel column chromatography (chloroform-acetone) to give 0.148 g (41%) of Compound (31) as colorless crystals.

$^1$H-NMR (CDCl$_3$) δ: 1.16 (d, 1H, J=8.2 Hz), 3.73 (s, 3H), 3.82 (s, 3H), 4.59–4.60 (m, 1H), 5.11 (d, 1H, J=8.2 Hz), 5.67 (s, 1H), 5.89 (s, 2H), 7.26–7.57 (m, 10H).

EXAMPLE 6

The compounds of the formula (VI) and (VII) of the present invention listed in the Tables 2 and 3 were obtained in substantially the same manners as those described in Process 2, Example 4 and Example 5 above.

TABLE 2

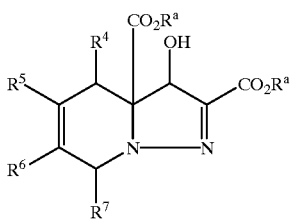
(VI)

| Compound No. | R$^a$ | R$^4$ | R$^7$ | R$^5$ | R$^6$ |
|---|---|---|---|---|---|
| 32 | t-Bu | H | H | Me | Me |
| 33 | n-Hex | H | H | Me | Me |
| 34 | Me | H | H | Me | Me |
| 35 | Et | H | H |  | Me |
| 36 | Me | H | H |  | Me |
| 37 | Et | —CH$_2$CH$_2$— |  | H | H |
| 38 | Me | H | H | H | H |
| 39 | Me | 3-Py | H | H | H |
| 40 | Me | 3-Py | 3-Py | H | H |
| 41 | Me | Me | Me | H | H |
| 42 | Me | n-Hex | n-Hex | H | H |
| 43 | Et | OAc | H | H | H |
| 44 | Et | H | OMe | H | H |
| 45 | Et | OMe | H | H | H |
| 46 | t-Bu | Ph | Ph | H | H |
| 47 | Et | Ph | Ph | H | H |
| 48 | Me | Ph-m-NO$_2$ | Ph-m-NO$_2$ | H | H |
| 49 | Me | Ph-p-Cl | Ph-p-Cl | H | H |
| 50 | Me | Ph-p-CN | Ph-p-CN | H | H |
| 51 | Me | Ph-p-COMe | Ph-p-COMe | H | H |
| 52 | Me | Ph-p-Me | Ph-p-Me | H | H |
| 53 | Me | Ph-p-NO$_2$ | Ph-p-NO$_2$ | H | H |
| 54 | Me | Ph-p-OMe | Ph-p-OMe | H | H |
| 55 | Me | Ph-p-Ph | Ph-p-Ph | H | H |

TABLE 3

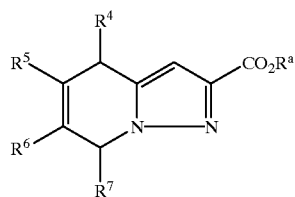
(VII)

| Compound No. | R$^a$ | R$^4$ | R$^7$ | R$^5$ | R$^6$ |
|---|---|---|---|---|---|
| 56 | t-Bu | H | H | Me | Me |
| 57 | n-Hex | H | H | Me | Me |
| 58 | Me | H | H | Me | Me |
| 59 | Et | H | H |  | Me |
| 60 | Me | H | H |  | Me |
| 61 | Et | —CH$_2$CH$_2$— |  | H | H |
| 62 | Me | H | H | H | H |
| 63 | Me | 3-Py | H | H | H |
| 64 | Me | 3-Py | 3-Py | H | H |
| 65 | Me | Me | Me | H | H |
| 66 | Et | H | OMe | H | H |
| 67 | Me | n-Hex | n-Hex | H | H |
| 68 | Et | OAc | H | H | H |
| 69 | Et | OMe | H | H | H |
| 70 | t-Bu | Ph | Ph | H | H |
| 71 | Me | Ph | Ph | H | H |
| 72 | Et | Ph | Ph | H | H |
| 73 | Me | Ph-m-NO$_2$ | Ph-m-NO$_2$ | H | H |
| 74 | Me | Ph-p-Cl | Ph-p-Cl | H | H |
| 75 | Me | Ph-p-CN | Ph-p-CN | H | H |
| 76 | Me | Ph-p-COMe | Ph-p-COMe | H | H |
| 77 | Me | Ph-p-Me | Ph-p-Me | H | H |
| 78 | Me | Ph-p-NO$_2$ | Ph-p-NO$_2$ | H | H |
| 79 | Me | Ph-p-OMe | Ph-p-OMe | H | H |
| 80 | Me | Ph-p-Ph | Ph-p-Ph | H | H |

The following are physiochemical data of the representative compounds listed in Tables 2 and 3.

Compound No. 32:
$^1$H-NMR (CDCl$_3$) δ: 1.42 (s, 9H), 1.55 (s, 9H), 1.62 (s, 3H), 1.70 (s, 3H), 2.33 (d, 1H, J=16.8 Hz), 2.75 (d, 1H, J=16.8 Hz), 2.85 (d, 1H, J=3.0 Hz), 4.08 (s, 2H), 5.19 (d, 1H, J=3.0 Hz)

Compound No. 33:
$^1$H-NMR (CDCl$_3$) δ: 0.86–0.91 (6H, m), 1.23–1.39 (12H, m), 1.54–1.82 (10H, m), 2.43 (d, 1H, J=16.8 Hz), 2.84 (d, 1H, J=16.8 Hz), 2.94 (d, 1H, J=3.9 Hz), 4.14–4.09 (4H, m), 4.24 (t, 2H, J=6.9 Hz), 5.17 (d, 1H, J=3.9 Hz)

Compound No. 34:
$^1$H-NMR (CDCl$_3$) δ: 1.64 (s, 3H), 1.70 (s, 3H), 2.44 (d, 1H, J=17.0 Hz), 2.87 (d, 1H, J=17.0 Hz), 2.97 (d, 1H, J=3.3 Hz), 3.73 (s, 3H), 3.85 (s, 3H), 4.03–4.18 (m, 2H), 5.18 (d, 1H, J=3.3 Hz).

Compound No. 35:
$^1$H-NMR (CDCl$_3$) δ: 1.25 (t, 3H, J=6.9 Hz), 1.35 (t, 3H, J=6.9 Hz), 1.71 (s, 1.5H), 1.77 (s, 1.5H), 2.46–2.61 (m, 1H), 2.80–2.88 (m, 2H), 4.09–4.37 (m, 6H), 5.17 (s, 1H), 5.40–5.52 (m, 1H).

Compound No. 36:
$^1$H-NMR (CDCl$_3$) δ: 1.71 (s, 1.5H), 1.77 (s, 1.5H), 2.45–2.63 (m, 1H), 2.87 (d, 1H, J=17.2 Hz), 3.73 (s, 1.5H), 3.84 (s, 1.5H), 4.08–4.24 (m, 2H), 5.15 (s, 1H), 5.41–5.49 (m, H).

Compound No. 37:
$^1$H-NMR (CDCl$_3$) δ: 1.14–1.38 (m, 7H), 1.45–1.61 (m, 2H), 2.13–2.25 (m, 1H), 3.18–3.31 (m, 2H), 4.19–4.39 (m, 4H), 4.61–4.68 (m, 1H), 5.03 (d, 1H, J=5.6 Hz), 6.00 (dd, 1H, J$_1$=7.2 Hz, J$_2$=5.5 Hz), 6.45 (dd, 1H, J$_1$=7.2 Hz, J$_3$=7.2 Hz).

Compound No. 38:
$^1$H-NMR (CDCl$_3$) δ: 2.68 (dd, 1H, J=5.6 & 17.2 Hz), 2.90–2.96 (m, 2H), 3.74 (s, 3H), 3.85 (s, 3H), 4.26–4.38 (m, 2H), 5.15 (d, 1H, J=3.6 Hz), 5.71–5.87 (m, 2H).

Compound No. 39:
$^1$H-NMR (D$_2$O) δ: 3.74 (s, 3H), 3.80 (s, 3H), 4.41–4.72 (m, 2H), 4.85 (d, 1H, J=6.9 Hz), 5.29 (s, 1H), 5.96–6.02 (m, 1H), 6.10–6.14 (m, 1H), 7.88–7.93 (m, 1H), 8.47 (d, 1H, J=8.3 Hz), 8.60–8.66 (m, 2H).

Compound No. 40:
$^1$H-NMR (D$_2$O) δ: 3.62 (s, 3H), 3.73 (s, 3H), 4.96 (dd, 1H, J=2.0 & 5.6 Hz), 5.19 (s, 1H), 5.83 (d, 1H, J=2.3 Hz), 5.98 (ddd, 1H, J=2.3, 5.6 & 9.9 Hz), 6.09 (dd, 1H, J=2.3 & 9.9 Hz), 7.79–8.89 (m, 8H).

Compound No. 41:
$^1$H-NMR (CDCl$_3$) δ: 1.29 (d, 3H, J=6.6 Hz), 1.52 (d, 3H, J=6.9 Hz), 2.75 (d, 1H, J=4.3 Hz), 3.24–3.34 (m, 1H), 3.69 (s, 3H), 3.85 (s, 3H), 4.46–4.48 (m, 1H), 5.26 (d, 1H, J=4.3 Hz), 5.52 (dd, 1H, J=3.0 & 10.2 Hz), 5.54–5.86 (m, 1H).

Compound No. 42:
$^1$H-NMR (CDCl$_3$) δ: 0.84–0.91 (m, 6H), 1.26–1.36 (m, 17H), 1.70–1.80 (m, 1H), 2.09–2.19 (m, 1H), 2.33–2.41 (m, 1H), 2.55–2.63 (m, 1H), 3.18–3.25 (m, 1H), 3.67 (s, 3H), 3.84 (s, 3H), 4.33–4.36 (m, 1H), 5.23 (d, 1H, J=4.6 Hz), 5.68 (dd, 1H, J=2.3 & 10.6 Hz), 5.96 (ddd, 1H, J=1.7, 6.3 & 10.6 Hz).

Compound No. 43:
$^1$H-NMR (CDCl$_3$) δ: 1.27 (t, 3H, J=6.9 Hz), 1.35 (t, 3H, J=6.9 Hz), 1.96 (s, 3H), 3.09 (brs, 1H), 4.18–4.47 (m, 6H), 5.34–5.40 (m, 2H), 5.89–6.09 (m, 2H).

Compound No. 45:
$^1$H-NMR (CDCl$_3$) δ: 1.25 (t, 3H, J=7.3 Hz), 1.35 (t, 3H, J=7.3 Hz), 3.35 (s, 3H), 4.13–4.25 (m, 2H), 4.28–4.37 (m, 2H), 4.42–4.56 (m, 2H), 4.80 (d, 1H, J=4.6 Hz), 4.88 (d, 1H, J=10.2 Hz), 5.31 (d, 1H, J=10.2 Hz), 6.07–6.20 (m, 2H).

Compound No. 46:
$^1$H-NMR (CDCl$_3$) δ: 0.98 (d, 1H, J=8.9 Hz), 1.43 (s, 9H), 1.51 (s, 9H), 4.52 (dd, 1H, J=2.3 & 4.6 Hz), 4.99 (d, 1H, J=8.9 Hz), 5.63–5.65 (m, 1H), 5.87–5.94 (m, 2H), 7.35–7.58 (m, 10H).

Compound No. 47:
$^1$H-NMR (CDCl$_3$) δ: 1.14 (d, 1H, J=7.9 Hz), 1.24 (t, 3H, J=7.3 Hz), 1.33 (t, 3H, J=7.3 Hz), 4.14–4.34 (m, 4H), 4.57–4.59 (m, 1H), 5.09 (d, 1H, J=7.9 Hz), 5.69 (d, 1H, J=2.0 Hz), 5.86–5.94 (m, 2H), 7.27–7.58 (m, 10H).

Compound No. 48:
$^1$H-NMR (CDCl$_3$) δ: 1.72 (d, 0.5H, J=6.3 Hz), 3.44 (d, 0.5H, J=1.7 Hz), 3.74 (s, 1.5H), 3.75 (s, 1.5H), 3.86 (s, 1.5H), 3.89 (s, 1.5H), 4.72–4.73 (m, 0.5H), 4.82 (dd, J=2.3 & 5.3 Hz), 4.87 (d, 0.5H, J=1.7 Hz), 5.16 (d, 0.5H, J=1.7 Hz), 5.49 (d, 0.5H, J=2.0 Hz), 5.81 (s, 0.5H), 5.95–6.08 (m, 2H), 7.41–8.40 (m, 8H).

Compound No. 49:
$^1$H-NMR (CDCl$_3$) δ: 1.30 (d, 1H, J=7.6 Hz), 3.74 (s, 3H), 3.81 (s, 3H), 4.54–4.57 (m, 1H), 5.11 (d, 1H, J=7.6 Hz), 5.62 (s, 1H), 5.82–5.92 (m, 2H), 7.23–7.47 (m, 8H).

Compound No. 50:
$^1$H-NMR (CDCl$_3$) δ: 1.68 (d, 1H, J=6.3 Hz), 3.76 (s, 3H), 3.84 (s, 3H), 4.62–4.64 (m, 1H), 5.13 (d, 1H, J=6.3 Hz), 5.72 (s, 1H), 5.89–5.90 (m, 2H), 7.49 (d, 2H, J=8.6 Hz), 7.55 (d, 2H, J=8.6 Hz), 7.63 (d, 2H, J=8.6 Hz), 7.75 (d, 2H, J=8.6 Hz).

Compound No. 51:
$^1$H-NMR (CDCl$_3$) δ: 1.51 (d, 1H, J=7.3 Hz), 2.57 (s, 3H), 2.65 (s, 3H), 3.74 (s, 3H), 3.84 (s, 3H), 4.66 (d, 1H, J=4.3 Hz), 5.14 (d, 1H, J=7.3 Hz), 5.75 (s, 1H), 5.86–5.95 (m, 2H), 7.54 (d, 2H, J=8.2 Hz), 7.65 (d, 2H, J=8.2 Hz), 7.87 (d, 2H, J=8.2 Hz), 8.05 (d, 2H, J=8.2 Hz).

Compound No. 52:
$^1$H-NMR (CDCl$_3$) δ: 1.20 (d, 1H, J=8.3 Hz), 2.31 (s, 3H), 2.39 (s, 3H), 3.72 (s, 3H), 3.81 (s, 3H), 4.55–4.57 (m, 1H), 5.09 (d, 1H, J=8.3 Hz), 5.62 (s, 1H), 5.83–5.87 (m, 2H), 7.12 (d, 2H, J=8.3 Hz), 7.25 (d, 2H, J=8.3 Hz), 7.39 (d, 2H, J=7.9 Hz), 7.44 (d, 2H, J=7.9 Hz).

Compound No. 53:
$^1$H-NMR (CDCl$_3$) δ: 1.73 (d, 1H, J=5.9 Hz), 3.76 (s, 3H), 3.86 (s, 3H), 4.71–4.72 (m, 1H), 5.16 (d, 1H, J=5.9 Hz), 5.79 (s, 1H), 5.90–5.93 (m, 2H), 7.56 (d, 2H, J=8.9 Hz), 7.71 (d, 2H, J=8.9 Hz), 8.11 (d, 2H, J=8.9 Hz), 8.33 (d, 2H, J=8.9 Hz).

Compound No. 54:
$^1$H-NMR (CDCl$_3$) δ: 1.21 (d, 1H, J=8.3 Hz), 3.73 (s, 3H), 3.77 (s, 3H), 3.81 (s, 3H), 3.85 (s, 3H), 4.53–4.55 (m, 1H), 5.09 (d, 1H, J=8.3 Hz), 5.59–5.61 (m, 1H), 5.82–5.92 (m, 2H), 6.83 (d, 2H, J=8.6 Hz), 6.97 (d, 2H, J=8.9 Hz), 7.40 (d, 2H, J=8.9 Hz), 7.47 (d, 2H, J=8.6 Hz).

Compound No. 71:
$^1$H-NMR (CDCl$_3$) δ: 3.87 (s, 3H), 4.90–4.92 (m, 1H), 5.92–5.94 (m, 1H), 6.02–6.08 (m, 1H), 6.99 (s, 1H), 7.16–7.35 (m, 10H).

EXAMPLE 7

The compounds of the formula (VIII) of the present invention listed in Table 4 were obtained in substantially the same manner as that described in Process 3.

TABLE 4

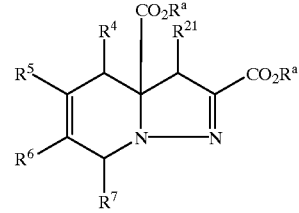

(VIII)

| Compound No. | R$^a$ | R$^{21}$ | R$^4$ | R$^7$ | R$^5$ | R$^6$ |
|---|---|---|---|---|---|---|
| 81 | Et | NH$_2$ | H | H | Me | Me |
| 82 | Et | SH | H | H | Me | Me |
| 83 | Et | OAc | H | H | Me | Me |
| 84 | Et | SH | H | H | | Me |
| 85 | Et | OAc | H | H | | Me |
| 86 | Et | NH$_2$ | —CH$_2$CH$_2$— | | H | H |
| 87 | Me | NH$_2$ (α) | H | H | H | H |
| 88 | Et | SH | 3-Py | H | H | H |
| 89 | Et | NH$_2$ | 3-Py | 3-Py | H | H |
| 90 | Me | NEt$_2$ | Me | Me | H | H |
| 91 | Et | SH | H | OMe | H | H |
| 92 | Me | SH | OAc | H | H | H |
| 93 | Me | OAc | OMe | H | H | H |
| 94 | Me | NH$_2$ (α) | Ph | Ph | H | H |
| 95 | Et | SH | Ph | Ph | H | H |
| 96 | n-Hex | NH$_2$ (β) | Ph-p-Cl | Ph-p-Cl | H | H |
| 97 | Me | SH | Ph-p-CN | Ph-p-CN | H | H |
| 98 | Et | OAc | Ph-p-COMe | Ph-p-COMe | H | H |
| 99 | Me | NH$_2$ (α) | Ph-p-Me | Ph-p-Me | H | H |
| 100 | Me | SH | Ph-p-NO$_2$ | Ph-p-NO$_2$ | H | H |
| 101 | Et | OAc | Ph-p-OMe | Ph-p-OMe | H | H |
| 102 | n-Pr | SH | Ph-p-Ph | Ph-p-Ph | H | H |

The following are physiochemical data of the representative compounds listed in Table 4.

Compound No. 81:
$^1$H-NMR (CDCl$_3$) δ: 1.26–1.40 (6H, m), 1.60 (3H, s), 1.64 (3H, s), 2.35–2.56 (2H, m), 4.02–4.19 (2H, m), 4.34–4.44 (4H, m), 4.71 (1H, s), 8.65 (3H, s).

Compound No. 82:

¹H-NMR (CDCl₃) δ: 1.21 (t, 1.5H, J=7.0 Hz), 1.28–1.38 (4.5H, m), 1.57–1.59 (3H, m), 1.65 (1.5H, S), 1.71 (1.5H, s), 1.96 (d, 0.5H, J=8.5 Hz), 2.10 (d, 0.5H, J=9.9 Hz), 2.26 (d, 0.5H, J=16.1 Hz), 2.40 (d, 0.5H, J=16.1 Hz), 2.53 (d, 0.5H, J=16.4 Hz), 3.00 (d, 0.5H, J=16.4 Hz), 4.05 (d, 0.5H, J=9.9 Hz), 4.11–4.37 (4H, m), 4.46 (d, 0.5H, J=8.5 Hz).

Compound No. 83:

¹H-NMR (CDCl₃) δ: 1.25 (t, 3H, J=7.3 Hz), 1.32 (t, 3H, J=7.3 Hz), 1.64 (s, 3H), 1.70 (s, 3H), 2.13 (s, 3H), 2.40–2.49 (m, 2H), 4.14–4.35 (m, 6H), 6.27 (s, 1H).

Compound No. 94:

¹H-NMR (D₂O) δ: 3.73 (s, 3H), 4.00 (s, 3H), 4.54 (s, 1H), 4.64 (s, 1H), 5.65 (s, 1H), 6.07 (s, 2H), 7.46–7.60 (m, 10H).

EXAMPLE 8

The compounds of the formula (X) of the present invention listed in Table 5 were obtained in substantially the same manner as that described in Process 4.

TABLE 5

(X)

| Compound No. | R¹¹ | R²² | R³¹ | R⁴ | R⁷ | R⁵ | R⁶ |
|---|---|---|---|---|---|---|---|
| 103 | CH₂OH | OH | CH₂OH | H | H | Me | Me |
| 104 | CH₂OH | OH | COOEt | H | H | Me | Me |
| 105 | CO₂Et | OH | CH₂OH | H | H | Me | Me |
| 106 | CH₂OH | OH | COO-n-Pr | H | H | Me | Me |
| 107 | CH₂OH | OH | COO-t-Bu | —CH₂CH₂— | | H | H |
| 108 | CH₂OH | SH | COO-t-Bu | H | H | H | H |
| 109 | COO-n-Pr | OH | CH₂OH | 3-Py | 3-Py | H | H |
| 110 | COO-t-Bu | OH | CH₂OH | Me | Me | H | H |
| 111 | CH₂OH | OH | COO-n-Pr | H | OMe | H | H |
| 112 | CH₂OH | OH | COO-t-Bu | n-Hex | n-Hex | H | H |
| 113 | COOEt | NH₂ | CH₂OH | OAc | H | H | H |
| 114 | COOEt | SH | CH₂OH | OMe | H | H | H |
| 115 | CH₂OH | OH | COOMe | Ph | Ph | H | H |
| 116 | CH₂OH | NEt₂ | COOMe | Ph | Ph | H | H |
| 117 | CH₂OH | OH | COO-n-Hex | Ph-p-Cl | Ph-p-Cl | H | H |
| 118 | CH₂OH | NH₂ | COO-n-Pr | Ph-p-CN | Ph-p-CN | H | H |
| 119 | CH₂OH | OH | COO-n-Pr | Ph-p-COMe | Ph-p-COMe | H | H |
| 120 | CH₂OH | OH | CH₂OH | Ph-p-Me | Ph-p-Me | H | H |
| 121 | CH₂OH | OH | COOEt | Ph-p-NO₂ | Ph-p-NO₂ | H | H |
| 122 | CH₂OH | NH₂ | CH₂OH | Ph-p-OMe | Ph-p-OMe | H | H |
| 123 | CH₂OH | SH | CH₂OH | Ph-p-Ph | Ph-p-Ph | H | H |

The following are physiochemical data of the representative compounds listed in Table 5.

Compound No. 103:

¹H-NMR (CDCl₃) δ: 1.25 (d, 1H, J=18.4 Hz), 1.59 (3H, s), 1.62 (3H, s), 2.47 (d, 1H, J=18.4 Hz), 3.42 (d, 1H, J=12.2 Hz), 3.58–3.76 (3H, m), 4.21–4.39 (5H, m), 5.20 (1H, s).

Compound No. 104:

¹H-NMR (CDCl₃) δ: 1.26 (t, 3H, J=7.0 Hz), 1.61 (3H, s), 1.67 (3H, s), 2.09 (d, 1H, J=16.8 Hz), 2.51–2.70 (2H, m), 3.13 (1H, s), 3.75–3.92 (2H, m), 4.20 (q, 2H, J=6.9 Hz), 4.40 (2H, s), 5.18 (1H, s).

Compound No. 105:

¹H-NMR (CDCl₃) δ: 1.35 (t, 3H, J=7.2 Hz), 1.62–1.73 (7H, m), 1.93 (1H, s), 2.76 (d, 1H, J=17.4 Hz), 3.23 (1H, s),
3.55–3.66 (2H, m), 3.88 (d, 1H, J=17.4 Hz), 4.08 (d, 1H, J=17.4 Hz), 4.32 (q, 2H, J=7.2 Hz), 5.35 (1H, s).

Compound No. 115:

¹H-NMR (CDCl₃) δ: 1.68 (brs, 2H), 3.81 (s, 3H), 4.30 (s, 2H), 4.56 (dd, 1H, J=2.6 & 5.0 Hz), 4.81 (s, 1H), 5.50 (d, 1H, J=2.0 Hz), 5.77–5.89 (m, 2H), 7.28–7.60 (m, 10H).

EXAMPLE 9

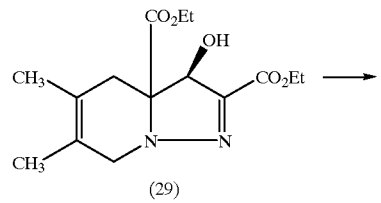

(29)

-continued

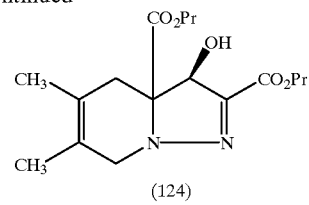

(124)

To a solution of 310 mg (1 mmol) of Compound (29) in 10 ml of propanol was added 142 mg (0.5 mmol) of Ti[OCH(CH₃)₂]₄ and the reaction mixture was refluxed for 18 hours under nitrogen gas atmosphere. After the reaction mixture was cooled to the room temperature and the solvent was removed under reduced pressure. The resulting residue was purified by silica gel column chromatography (chloroform-acetone) to give 230 mg (68%) of Compound (124) as pale yellowish crystals.

$^1$H-NMR (CDCl$_3$) δ: 0.90 (t, 3H, J=7.6 Hz), 0.96 (t, 3H, J=7.6 Hz), 1.56–1.82 (10H, m), 2.43 (d, 1H, J=16.8 Hz), 2.82–2.88 (m, 2H), 4.06–4.11 (4H, m), 4.21 (t, 2H, J=6.9 Hz), 5.19 (d, 1H, J=3.6 Hz).

EXAMPLE 10

The compounds of the formula (XI) of the present invention listed in Table 6 were obtained in substantially the same manners as those described in Process 5 and Example 9 above.

Compound No. 127:
$^1$H-NMR (CDCl$_3$) δ: 1.26 (t, 3H, J=7.3 Hz), 1.59 (d, 3H, J=6.9 Hz), 1.64 (s, 3H), 1.71 (s, 3H), 2.05 (s, 1H), 2.46 (d, 1H, J=16.2 Hz), 2.89 (brd, 1H, J=17.2 Hz), 3.12 (d, 1H, J=3.0 Hz), 3.77 (s, 3H), 4.11–4.23 (m, 4H), 5.22 (d, 1H, J=3.0 Hz), 5.36 (q, 1H, J=6.9 Hz).

Compound No. 128:
$^1$H-NMR (CDCl$_3$) δ: 1.24 (t, 3H, J=7.3 Hz), 1.59 (d, 3H, J=6.9 Hz), 1.63 (s, 1H), 1.71 (s, 1H), 2.05 (s, 1H), 2.46 (d, 1H, J=16.8 Hz), 2.71 (d, 1H, J=4.0 Hz), 2.87 (brd, 1H, J=17.2 Hz), 3.76 (s, 3H), 4.14–4.23 (m, 2H), 5.21 (d, 1H, J=4.0 Hz), 5.28 (q, 1H, J=6.9 Hz).

Compound No. 129:
$^1$H-NMR (DMSO-d$_6$) δ: 1.13 (t, 3H, J=7.3 Hz), 1.61 (s, 3H), 1.66 (s, 3H), 2.32 (d, 1H, J=16.8 Hz), 2.69 (d, 1H, J=16.8 Hz), 3.98 (s, 2H), 4.05–4.13 (m, 2H), 4.73 (s, 1H).

TABLE 6

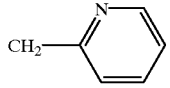

(XI)

| Compound No. | R$^c$ | R$^2$ | R$^b$ | R$^4$ | R$^7$ | R$^5$ | R$^6$ |
|---|---|---|---|---|---|---|---|
| 125 | n-Pr | OH (β) | n-Pr | H | H | Me | Me |
| 126 | n-Pr | OH (α) | n-Pr | H | H | Me | Me |
| 127 | CH(Me)COOMe | OH (α) | Et | H | H | Me | Me |
| 128 | CH(Me)COOMe | OH (β) | Et | H | H | Me | Me |
| 129 | H | OH | Et | H | H | Me | Me |
| 130 | CH$_2$-(2-pyridyl) | OH | H | H | H | Me | Me |
| 131 | H | OH | Et | —CH$_2$CH$_2$— | | H | H |
| 132 | H | OAc | Me | Ph | Ph | H | H |
| 133 | CH$_2$CH$_2$N(Me)$_2$ | OH | Me | Ph | Ph | H | H |
| 134 | CH(Me)COOMe | OAc | Et | 3-Py | H | H | H |
| 135 | CH$_2$CH$_2$N(Me)$_2$ | NH$_2$ | Me | 3-Py | 3-Py | H | H |
| 136 | CH$_2$CH$_2$NO$_2$ | NH$_2$ | Et | Me | Me | H | H |
| 137 | H | OH | H | H | OMe | H | H |
| 138 | H | OH | Et | OAc | H | H | H |
| 139 | n-Pr | OH | Et | Ph | Ph | H | H |
| 140 | n-Pr | OH | Me | Ph | Ph | H | H |
| 141 | H | OAc | Me | Ph-p-CN | Ph-p-CN | H | H |
| 142 | CH(Me)COOMe | OH | Et | Ph-p-COMe | Ph-p-COMe | H | H |
| 143 | n-Pr | OH | Et | Ph-p-Me | Ph-p-Me | H | H |
| 144 | H | OH | H | Ph-p-OMe | Ph-p-OMe | H | H |
| 145 | H | OH | Et | Ph-p-Ph | Ph-p-Ph | H | H |

The following are physiochemical data of the representative compounds listed in Table 6.

Compound No. 125:
$^1$H-NMR (CDCl$_3$) δ: 0.91 (t, 3H, J=7.9 Hz), 0.97 (t, 3H, J=7.9 Hz), 1.63 (brs, 3H), 1.70 (brs, 3H), 1.60–1.80 (m, 4H), 2.44 (d, 1H, J=16.8 Hz), 2.82–2.92 (m, 2H), 4.07–4.12 (m, 6H), 4.22 (t, 2H, J=6.9 Hz), 5.19 (d, 1H, J=4.0 Hz).

Compound No. 126:
$^1$H-NMR (CDCl$_3$) δ: 0.90 (t, 3H, J=7.3 Hz), 0.97 (t, 3H, J=7.6 Hz), 1.44 (brs, 3H), 1.47 (brs, 3H), 1.57–1.82 (m, 4H), 2.45 (d, 1H, J=16.5 Hz), 2.86 (brd, 1H, J=16.8 Hz), 3.22 (d, 1H, J=4.3 Hz), 4.07–4.10 (m, 6H), 4.21 (t, 2H, J=5.6 Hz), 5.18 (d, 1H, J=4.3 Hz).

Compound No. 132:
$^1$H-NMR (CDCl$_3$) δ: 1.08 (s, 3H), 3.87 (s, 3H), 4.42 (dd, 1H, J=2.3 & 6.3 Hz), 5.62 (d, 1H, J=2.3 Hz), 5.77 (dd, 1H, J=2.3 & 9.9 Hz), 5.91 (ddd, 1H, J=2.3, 5.9 & 9.9 Hz), 6.17 (s, 1H), 7.18–7.64 (m, 10H).

Compound No. 133:
$^1$H-NMR (D$_2$O) δ: 2.75 (s, 6H), 3.33–3.36 (m, 2H), 3.75 (s, 3H), 4.36–4.40 (m, 2H), 4.58–4.64 (m, 1H), 5.18 (s, 1H), 5.54 (s, 1H), 5.79 (s, 2H), 7.19–7.54 (m, 10H).

Compound No. 139:
$^1$H-NMR (CDCl$_3$) δ: 0.88 (t, 3H, J=7.3 Hz), 1.20 (d, 1H, J=8.2 Hz), 1.33 (t, 3H, J=6.9 Hz), 1.57–1.70 (m, 2H), 4.09 (t, 2H, J=6.9 Hz), 4.19–4.36 (m, 2H), 4.58 (s, 1H), 5.08 (d, 1H, J=8.2 Hz), 5.69 (s, 1H), 5.90 (d, 2H, J=2.6 Hz), 7.25–7.57 (m, 10H).

Compound No. 140:

$^1$H-NMR (CDCl$_3$) δ: 0.88 (t, 3H, J=7.3 Hz), 1.11 (d, 1H, J=8.3 Hz), 1.57–1.71 (m, 2H), 3.82 (s, 3H), 4.09 (t, 2H, J=6.9 Hz), 4.58–4.60 (m, 1H), 5.08 (d, 1H, J=8.3 Hz), 5.68 (s, 1H), 5.89–5.90 (m, 2H), 7.28–7.58 (m, 10H).

EXAMPLE 11

The compounds of the formula (XII) of the present invention listed in Table 7 were obtained in substantially the same manner as that described in Process 5.

The following are physiochemical data of the representative compounds listed in Table 7.

Compound No. 146:

$^1$H-NMR (CDCl$_3$) δ: 1.00 (t, 3H, J=7.4 Hz), 1.77–1.87 (8H, m), 3.21–3.32 (2H, m), 4.33 (t, 2H, J=6.9 Hz), 4.52–4.53 (2H, m), 7.00 (1H, s).

TABLE 7

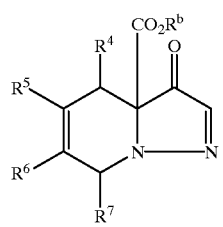

(XII)

| Compound No. | R$^a$ | R$^4$ | R$^7$ | R$^5$ | R$^6$ |
|---|---|---|---|---|---|
| 146 | n-Pr | H | H | Me | Me |
| 147 | H | H | H | Me | Me |
| 148 | Et | H | —CH$_2$CH$_2$— | H | H |

TABLE 7-continued

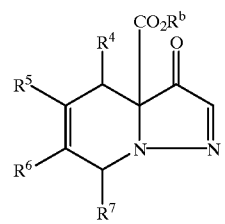

(XII)

| Compound No. | R$^a$ | R$^4$ | R$^7$ | R$^5$ | R$^6$ |
|---|---|---|---|---|---|
| 149 | Et | H | H | H | H |
| 150 | Me | Ph | Ph | H | H |
| 151 | Et | 3-Py | H | H | H |
| 152 | Me | 3-Py | 3-Py | H | H |
| 153 | Et | Me | Me | H | H |
| 154 | H | H | OMe | H | H |
| 155 | Et | OAc | H | H | H |
| 156 | Me | OMe | H | H | H |
| 157 | Et | Ph | Ph | H | H |
| 158 | n-Pr | Ph-p-Cl | Ph-p-Cl | H | H |
| 159 | Me | Ph-p-CN | Ph-p-CN | H | H |
| 160 | Et | Ph-p-COMe | Ph-p-COMe | H | H |
| 161 | Et | Ph-p-Me | Ph-p-Me | H | H |
| 162 | H | Ph-p-OMe | Ph-p-OMe | H | H |
| 163 | Et | Ph-p-Ph | Ph-p-Ph | H | H |

EXAMPLE 12

The compounds of the formula (XIV) of the present invention listed in Table 8 were obtained in substantially the same manner as that described in Process 6.

TABLE 8

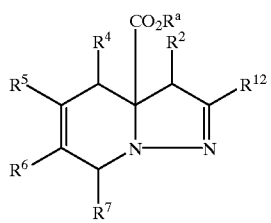

(XIV)

| Compound No. | R$^{12}$ | R$^2$ | R$^a$ | R$^4$ | R$^7$ | R$^5$ | R$^6$ |
|---|---|---|---|---|---|---|---|
| 164 | CN | OH | n-Pr | H | H | Me | Me |
| 165 | CONEt$_2$ | NH$_2$ | Et | H | —CH$_2$CH$_2$— | H | H |
| 166 | COMe | OH | Me | Ph | Ph | H | H |
| 167 | COCH$_2$NO$_2$ | OH | CO$_2$Me | Ph | Ph | H | H |
| 168 | CON⟨NCH$_3$⟩ | OH | Me | Ph | Ph | H | H |
| 169 | CN | OH | Me | Ph | Ph | H | H |

TABLE 8-continued

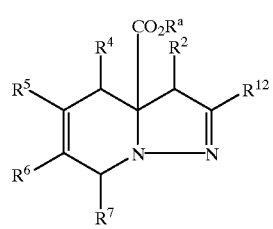

(XIV)

| Compound No. | R¹² | R² | Rᵃ | R⁴ | R⁷ | R⁵ | R⁶ |
|---|---|---|---|---|---|---|---|
| 170 | 4-(4,4-dimethyl-oxazolin-2-yl)phenyl-CO- | OH | Me | Ph | Ph | H | H |
| 171 | COCH₂-(2-pyridyl) | OH | Me | Ph | Ph | H | H |
| 172 | CONH₂ | OH | Me | Ph | Ph | H | H |
| 173 | CONEt₂ | OH | Me | Ph | Ph | H | H |
| 174 | CONHC(NH)NH₂ | OH | Me | Ph | Ph | H | H |
| 175 | CSNH₂ | OH | Me | Ph | Ph | H | H |
| 176 | CO-(imidazol-1-yl) | OH | Me | Ph | Ph | H | H |
| 177 | CO-(2-pyridyl) | OH | Me | Ph | Ph | H | H |
| 178 | COCH₂-(2-quinolyl) | OH | Me | Ph-p-Me | Ph-p-Me | H | H |

The following are physiochemical data of the representative compounds listed in Table 8.

Compound No. 164:
¹H-NMR (CDCl₃) δ: 0.91 (t, 3H, J=7.4 Hz), 1.58–1.71 (8H, m), 2.39 (d, 1H, J=16.5 Hz), 2.75–2.86 (2H, m), 4.01–4.17 (4H, m), 5.08 (d, 1H, J=7.2 Hz).

Compound No. 166:
¹H-NMR (CDCl₃) δ: 1.24 (d, 1H, J=6.9 Hz), 2.26 (s, 3H), 3.82 (s, 3H), 4.56–4.59 (m, 1H), 5.17 (d, 1H, J=6.9 Hz), 5.66 (s, 1H), 5.88–5.98 (m, 2H), 7.22–7.60 (m, 10H).

Compound No. 167:
¹H-NMR (CDCl₃) δ: 1.37 (d, 1H, J=7.9 Hz), 3.86 (s, 3H), 4.60 (dd, 1H, J=2.3 & 5.9 Hz), 5.26 (d, 1H, J=7.9 Hz), 5.42 & 5.60 (ABq, 2H, J=14.5 Hz), 5.67–5.68 (m, 1H), 5.91 (dd, 1H, J=2.3 & 10.9 Hz), 6.01 (ddd, 1H, J=2.3, 5.6 & 10.2 Hz), 7.27–7.54 (m, 10H).

Compound No. 168:
¹H-NMR (D₂O) δ: 2.84 (s, 3H), 2.89–3.28 (m, 4H), 3.84 (s, 3H), 4.50–4.71 (m, 4H), 5.25 (s, 1H), 5.55 (s, 1H), 5.87–5.96 (m, 2H), 7.23–7.62 (m, 10H).

Compound No. 169:
¹H-NMR (CDCl₃) δ: 1.09 (d, 1H, J=10.6 Hz), 3.87 (s, 3H), 4.59 (dd, 1H, J=2.3 & 5.6 Hz), 4.95 (d, 1H, J=10.6 Hz), 5.59–5.61 (m, 1H), 5.89 (dd, 1H, J=2.3 & 10.6 Hz), 5.97 (ddd, 1H, J=2.0, 5.6 & 10.6 Hz), 7.28–7.54 (m, 10H).

Compound No. 170:
¹H-NMR (CDCl₃) δ: 1.38 (s, 6H), 3.81 (s, 3H), 4.07–4.14 (m, 2H), 4.61–4.64 (m, 1H), 5.41 (s, 1H), 5.70 (d, 1H, J=2.3 Hz), 5.93 (dd, 1H, J=2.3 & 10.2 Hz), 6.02 (ddd, 1H, J=2.0, 5.6 & 10.2 Hz), 7.20–7.34 (m, 4H), 7.37–7.60 (m, 6H), 7.88 (d, 2H, J=8.6 Hz), 8.08 (d, 2H, J=8.6 Hz).

Compound No. 171:
¹H-NMR (CDCl₃) δ: 3.79 (s, 3H), 4.19 (s, 1H), 4.54–4.60 (m, 1H), 5.22 (s, 1H), 5.66–5.67 (m, 1H), 5.84–5.99 (m, 2H), 6.87–7.63 (m, 13H), 8.42 (d, 1H, J=4.0 Hz).

Compound No. 172:
¹H-NMR (CDCl₃) δ: 3.82 (s, 3H), 4.58 (s, 1H), 5.12 (brs, 1H), 5.18 (s, 1H), 5.60 (s, 1H), 5.83–5.87 (m, 2H), 6.25 (brs, 1H), 7.28–7.64 (m, 10H).

Compound No. 173:
¹H-NMR (CDCl₃) δ: 0.98 (t, 3H, J=6.9 Hz), 1.07 (t, 3H, J=7.3 Hz), 2.54 (d, 1H, J=3.6 Hz), 3.31 (q, 2H, J=6.9 Hz), 3.42–3.61 (m, 2H), 3.82 (s, 3H), 4.56 (dd, 1H, J=2.3 & 5.3 Hz), 5.15 (d, 1H, J=3.6 Hz), 5.56–5.57 (m, 1H), 5.86 (dd, 1H, J=2.0 & 10.6 Hz), 5.94 (ddd, 1H, J=2.3, 5.6 & 10.6 Hz), 7.22–7.57 (m, 10H).

Compound No. 174:
¹H-NMR (CDCl₃) δ: 3.75 (s, 3H), 4.56–4.58 (m,1H), 5.19 (s, 1H), 5.54 (s, 1H), 5.73–5.78 (m, 2H), 6.94 (s, 4H), 7.16–7.49 (m, 10H).

Compound No. 177:

$^1$H-NMR (CDCl$_3$) δ: 1.56 (brs, 1H), 3.66 (s, 3H), 4.43–4.45 (m, 1H), 4.79 (s, 1H), 5.49 (s, 1H), 5.77–5.86 (m, 2H), 7.08–7.63 (m, 12H), 8.34–8.37 (m, 2H).

EXAMPLE 13

The compounds of the formula (XV) of the present invention listed in Table 9 were obtained in substantially the same manner as that described in Process 7.

TABLE 9

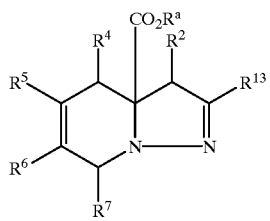

(XV)

| Compound No. | R$^{13}$ | R$^2$ | R$^a$ | R$^4$ | R$^7$ | R$^5$ | R$^6$ |
|---|---|---|---|---|---|---|---|
| 179 | 2-imidazolinyl (HN) | OH | Et | H | H | Me | Me |
| 180 | thiazoline-CO$_2$Et | OH | Me | H | H | Me | Me |
| 181 | 2-imidazolinyl (HN) | OH | Me | Ph | Ph | H | H |
| 182 | 1,3,4-thiadiazolyl | OH | Et | H | H | Me | Me |
| 183 | thiazolinyl | OH | H | H | H | Me | Me |
| 184 | oxazolinyl | OH | Me | Ph | Ph | H | H |
| 185 | 4,4-dimethyloxazolinyl | OH | Me | Ph | Ph | H | H |
| 186 | oxazoline-CO$_2$Me | OH | Me | Ph | Ph | H | H |
| 187 | 1,3,4-oxadiazolyl | OH | Me | Ph | Ph | H | H |

TABLE 9-continued (XV)

| Compound No. | R[13] | R[2] | R[a] | R[4] | R[7] | R[5] | R[6] |
|---|---|---|---|---|---|---|---|
| 188 | (triazolyl) | $NH_2$ | Et | Ph-m-$NO_2$ | Ph-m-$NO_2$ | H | H |
| 189 | (pyridyl) | $NH_2$ | Et | Ph-p-Cl | Ph-p-Cl | H | H |

The following are physiochemical data of the representative compounds listed in Table 9.

Compound No. 185:

$^1$H-NMR (CDCl$_3$) δ: 1.21 (s, 3H), 1.27 (s, 3H), 1.73 (brs, 1H), 3.82 (s, 1H), 3.94 (s, 2H), 4.58 (dd, 1H, J=2.3 & 4.6 Hz), 5.16 (s, 1H), 5.65 (d, 1H, J=2.0 Hz), 5.79–5.91 (m, 2H), 7.22–7.57 (m, 10H).

Compound No. 186:

$^1$H-NMR (CDCl$_3$) δ: 1.55 (brs, 1H), 3.74 (dd, 1H, J=4.0 & 11.5 Hz), 3.78 (s, 3H), 3.81 (s, 3H), 3.90 (dd, 1H, J=3.3 & 11.5 Hz), 4.57–4.59 (m, 1H), 4.91–4.96 (m, 1H), 5.17 (d, 1H, J=5.0 Hz), 5.62 (s, 1H), 5.85–5.94 (m, 2H), 7.14–7.60 (m, 10H).

Compound No. 187:

$^1$H-NMR (CDCl$_3$) δ: 1.38 (d, 1H, J=8.3 Hz), 3.80 (s, 3H), 4.63–4.65 (m, 1H), 5.31 (d, 1H, J=8.3 Hz), 5.69 (s, 1H), 5.89–5.95 (m, 2H), 7.25–7.62 (m, 10H), 8.58 (s, 1H).

EXAMPLE 14

The compounds of the formula (XVII) of the present invention listed in Table 10 were obtained in substantially the same manner as that described in Process 8.

TABLE 10

(XVII)

| Compound No | R[14] | R[22] | R[a] | R[4] | R[7] | R[5] | R[6] |
|---|---|---|---|---|---|---|---|
| 190 | $CH_2NH_2$ | OH | n-Pr | H | H | Me | Me |
| 191 | $CH_2SO$ (α) Me | OH | n-Pr | H | H | Me | Me |
| 192 | $CH_2SO$ (β) Me | OH | n-Pr | H | H | Me | Me |
| 193 | CH=C(CN)$_2$ | OH | n-Pr | H | H | Me | Me |
| 194 | CH=CH$_2$ | OH | n-Pr | H | H | Me | Me |
| 195 | CH=CHC$_6$H$_5$ | OH | n-Pr | H | H | Me | Me |
| 196 | CH=CHCN | OH | n-Pr | H | H | Me | Me |
| 197 | CH=CHCO$_2$Et | OH | n-Pr | H | H | Me | Me |
| 198 | CH=CHNO$_2$ | OH | nPr | H | H | Me | Me |
| 199 | CH(OH)CH$_2$NO$_2$ | OH | n-Pr | H | H | Me | Me |
| 200 | CH$_2$CH$_2$NO$_2$ | OH | n-Pr | H | H | Me | Me |
| 201 | CH(CH$_2$NO$_2$)CH(CN)$_2$ | OH | n-Pr | H | H | Me | Me |
| 202 | CH$_2$S(O)Me | OH | Me | Ph | H | H | H |
| 203 | CH$_2$SMe | OH | Me | Ph | Ph | H | H |
| 204 | CH$_2$SO$_2$Me | OH | Me | Ph | Ph | H | H |
| 205 | CH$_2$SOMe | OH | Me | Ph | Ph | H | H |
| 206 | CH=CHSO$_2$Me | OH | Me | Ph | Ph | H | H |
| 207 | CH(OH)CH$_2$NO$_2$ | OH | Me | Ph | Ph | H | H |

TABLE 10-continued (XVII)

| Compound No | R[14] | R[22] | R[a] | R[4] | R[7] | R[5] | R[6] |
|---|---|---|---|---|---|---|---|
| 208 | CH₂—N⟨azetidine⟩—OH | OH | Me | Ph | Ph | H | H |
| 209 | CH₂O—C₆H₄—CH₂COOH | OH | Me | Ph | Ph | H | H |
| 210 | CH=CHMe | OAc | Et | 3-Py | H | H | H |
| 211 | CH=CHMe | NH₂ | Et | 3-Py | 3-Py | H | H |
| 212 | —C≡C—Me | NH₂ | Et | Me | Me | H | H |
| 213 | CH₂OAc | OH | Me | Ph | Ph | H | H |

The following are physiochemical data of the representative compounds listed in Table 10.

Compound No. 190:
$^1$H-NMR (CDCl$_3$) δ: 0.91 (t, 3H, J=7.4 Hz), 1.01 (t, 3H, J=7.2 Hz), 1.42–1.74 (8H, m), 2.13 (d, 1H, J=17 Hz), 2.55 (d, 1H, J=17 Hz), 3.35 (1H, s), 3.66–3.88 (6H, m), 4.11 (t, 2H, J=6.6 Hz), 5.23 (1H, s).

Compound No. 191:
$^1$H-NMR (CDCl$_3$) δ: 0.92 (t, 3H, J=7.4 Hz), 1.59–1.72 (8H, m), 2.26 (d, 1H, J=16.8 Hz), 2.54 (3H, s), 2.70 (d, 1H, J=16.8 Hz), 3.50 (d, 1H, J=13.8 Hz), 3.84–3.97 (2H, m), 4.05–4.18 (3H, m), 4.89 (d, 1H, J=6.8 Hz), 5.55 (d, 1H, J=6.8 Hz).

Compound No. 192:
$^1$H-NMR (CDCl$_3$) δ: 0.92 (t, 3H, J=7.4 Hz), 1.61–1.68 (8H, m), 2.17 (d, 1H, J=16.8 Hz), 2.56 (d, 1H, J=16.8 Hz), 2.67 (3H, s), 3.60 (d, 1H, J=13.2 Hz), 3.80–3.95 (2H, m), 4.01–4.14 (3H, m), 4.89 (d, 1H, J=6.9 Hz), 5.10 (d, 1H, J=6.9 Hz).

Compound No. 193:
$^1$H-NMR (CDCl$_3$) δ: 0.91 (t, 3H, J=7.4 Hz), 1.58–1.75 (8H, m), 2.56 (d, 1H, J=16.8 Hz), 2.92–3.10 (2H, m), 4.09–4.35 (4H, m), 5.41 (d, 1H, J=6.9 Hz), 7.57 (1H, s).

Compound No. 194:
$^1$H-NMR (CDCl$_3$) δ: 0.91 (t, 3H, J=7.2 Hz), 1.60–1.68 (8H, m), 2.13 (d, 1H, J=6.3 Hz), 2.25 (d, 1H, J=16.8 Hz), 2.67 (d, 1H, J=16.8 Hz), 3.84–4.16 (4H, m), 5.12 (d, 1H, J=6.3 Hz), 5.35 (d, 1H, J=11.2 Hz), 5.69 (d, 1H, J=17.8 Hz), 6.51 (dd, 1H, J=11.2 & 17.8 Hz).

Compound No. 195:
$^1$H-NMR (CDCl$_3$) δ: 0.87–0.94 (3H, m), 1.32 (d, 0.5H, J=6.2 Hz), 1.57–1.68 (8H, m), 2.12 (d, 0.5H, J=17.1 Hz), 2.28–2.38 (1H, m), 2.53 (d, 0.5H, J=17.1 Hz), 2.73 (d, 0.5H, J=16.5 Hz), 3.87–4.02 (2H, m), 4.06–4.16 (2H, m), 4.84 (d, 0.5H, J=6.9 Hz), 6.35 (d, 0.5H, J=12.2 Hz), 6.72 (d, 0.5H, J=12.2 Hz), 6.92 (d, 0.5H, J=16.8 Hz), 7.03 (d, 0.5H, J=16.8 Hz), 7.20–7.43 (5H, m).

Compound No. 196:
$^1$H-NMR (CDCl$_3$) δ: 0.88–0.94 (3H, m), 1.59–1.72 (8H, m), 2.25–2.31 (1H, m), 2.50 (d, 0.5H, J=16.8 Hz), 2.68 (d, 0.5H, J=16.4 Hz), 2.82 (d, 0.5H, J=6.9 Hz), 2.89 (d, 0.5H, J=16.8 Hz), 3.95–4.17 (4H, m), 5.11–5.15 (1H, m), 5.44 (d, 0.5H, J=6.9 Hz), 5.68 (d, 0.5H, J=16.4 Hz), 6.99 (d, 0.5H, J=11.8 Hz), 7.14 (d, 0.5H, J=16.4 Hz).

Compound No. 197:
$^1$H-NMR (CDCl$_3$) δ: 0.90 (t, 3H, J=7.4 Hz), 1.29 (t, 3H, J=7.1 Hz), 1.60–1.69 (8H, m), 2.04–2.36 (2H, m), 2.71 (d, 1H, J=15.8 Hz), 4.01–4.25 (6H, m), 5.10 (d, 1H, J=5.9 Hz), 6.21 (d, 1H, J=16.1 Hz), 7.45 (d, 1H, J=16.1 Hz).

Compound No. 198:
$^1$H-NMR (CDCl$_3$) δ: 0.92 (t, 3H, J=7.4 Hz), 1.59–1.71 (8H, m), 2.31–2.39 (2H, m), 2.72 (d, 1H, J=16.2 Hz), 4.05–4.22 (4H, m), 5.17 (d, 1H, J=6.9 Hz), 7.44 (d, 1H, J=13.5 Hz), 7.82 (d, 1H, J=13.5 Hz).

Compound No. 199:
$^1$H-NMR (CDCl$_3$) δ: 0.92 (t, 3H, J=7.4 Hz), 1.62–1.69 (8H, m), 2.08 (d, 2H, J=16.3 Hz), 2.58 (d, 1H, J=16.3 Hz), 2.74 (1H, s), 3.27 (1H, s), 3.76–3.95 (2H, m), 4.05–4.19 (2H, m), 4.63–4.86 (2H, m), 5.16–5.29 (2H, m).

Compound No. 200:
$^1$H-NMR (CDCl$_3$) δ: 0.92 (t, 3H, J=7.4 Hz), 1.60–1.72 (m, 8H), 2.00 (d, 1H, J=16.8 Hz), 2.45–2.58 (m, 2H), 2.88–3.12 (m, 2H), 3.73–3.89 (m, 2H), 4.04–4.19 (m, 2H), 4.59–4.77 (m, 2H), 5.05 (s, 1H).

Compound No. 201:
$^1$H-NMR (CDCl$_3$) δ: 0.92 (t, 3H, J=7.4 Hz), 1.61–1.69 (m, 8H), 2.00–2.08 (m, 1H), 2.51–2.63 (m, 1H), 2.90–3.15 (m, 1H), 3.80–4.03 (m, 3H), 4.03–4.20 (m, 2H), 4.55 (d, 0.5H, J=7.2 Hz), 4.71–4.87 (m, 1.5H), 4.97–5.06 (m, 1H), 5.20 (d, 1H, J=10.2 Hz).

Compound No. 202:
$^1$H-NMR (CDCl$_3$) δ: 2.40 (s, 1.8H), 2.47 (s, 1.2H), 3.20 & 3.52 (ABq, 1.8H, J=13.9 Hz), 3.64–3.71 (m, 1.2H), 3.76 (s, 3H), 4.34–4.50 (m, 3H), 4.78 (d, 0.6H, J=5.9 Hz), 4.97 (d, 0.4H, J=7.3 Hz), 5.79–5.96 (m, 2H), 7.13–7.20 (m, 3H), 7.23–7.35 (m, 2H).

Compound No. 203:

$^1$H-NMR (CDCl$_3$) δ: 0.86 (d, 1H, J=9.6 Hz), 1.97 (s, 3H), 3.16 & 3.29 (ABq, 2H, J=14.2 Hz), 3.80 (s, 3H), 4.56 (dd, 1H, J=2.3 & 5.0 Hz), 4.90 (d, 1H, J=9.6 Hz), 5.53 (d, 1H, J=2.3 Hz), 5.77 (ddd, 1H, J=2.3, 5.3 & 10.2 Hz), 5.86 (dd, 1H, J=2.0 & 10.2 Hz), 7.28–7.60 (m, 10H).

Compound No. 204:

$^1$H-NMR (CDCl$_3$) δ: 0.94 (d, 1H, J=8.6 Hz), 2.85 (s, 3H), 3.78 & 3.99 (ABq, 2H, J=14.3 Hz), 3.83 (s, 3H), 4.58 (dd, 1H, J=2.6 & 5.6 Hz), 5.00 (d, 1H, J=8.6 Hz), 5.58 (d, 1H, J=2.0 Hz), 5.79 (dd, 1H, J=2.6 & 10.2 Hz), 5.83–5.91 (m, 1H), 7.26–7.59 (m, 10H).

Compound No. 205:

$^1$H-NMR (CDCl$_3$) δ: 1.45 (d, 0.3H, J=7.9 Hz), 2.44 (s, 2.1H), 2.48 (s, 0.9H), 3.10 (d, 0.7H, J=6.3 Hz), 3.27 & 3.90 (ABq, 0.6H, J=13.5 Hz), 3.60 & 3.80 (ABq, 1.4H, J=13.5 Hz), 3.80 (s, 3H), 4.56–4.59 (m, 1H), 4.65 (d, 0.7H, J=5.9 Hz), 4.88 (d, 0.3H, J=7.6 Hz), 5.52 (s, 0.7H), 5.61 (s, 0.3H), 5.75–5.88 (m, 2H), 7.19–7.60 (m, 10H).

Compound No. 206:

$^1$H-NMR (CDCl$_3$) δ: 0.95 (d, 1H, J=10.6 Hz), 2.86 (s, 3H), 3.85 (s, 3H), 4.60 (dd, 1H, J=2.3 & 5.0 Hz), 4.98 (d, 1H, J=10.6 Hz), 5.59 (d, 1H, J=1.7 Hz), 5.87–5.98 (m, 2H), 6.44 (d, 1H, J=15.5 Hz), 7.29–7.57 (m, 10H).

Compound No. 207:

$^1$H-NMR (CDCl$_3$) δ: 1.09 (d, 1H, J=8.9 Hz), 1.62 (brs, 1H), 3.82 (s, 2.4H), 3.84 (s, 0.6H), 4.48–4.69 (m, 3H), 4.90 (d, 1H, J=8.2 Hz), 5.02 (brs, 0.8H), 5.21 (d, 0.2H, J=6.9 Hz), 5.47–5.49 (m, 1H), 5.79–5.98 (m, 2H), 7.28–7.58 (m, 10H).

Compound No. 208:

$^1$H-NMR (CDCl$_3$) δ: 3.01–3.07 (m, 2H), 3.21 & 3.44 (ABq, 2H, J=13.5 Hz), 3.49–3.63 (m, 2H), 3.79 (s, 3H), 4.29–4.34 (m, 1H), 4.53 (dd, 1H, J=2.6 & 5.0 Hz), 4.79 (s, 1H), 5.48 (d, 1H, J=2.0 Hz), 5.74–5.86 (m, 2H), 7.25–7.58 (m, 10H).

Compound No. 209:

$^1$H-NMR (CDCl$_3$) δ: 3.50 (s, 3H), 3.55 (s, 2H), 4.52 (dd, 1H, J=2.3 & 5.3 Hz), 4.69 & 4.75 (ABq, 2H, J=13.2 Hz), 4.80 (s, 1H), 5.55 (d, 1H, J=2.3 Hz), 5.73–5.80 (m, 1H), 5.86 (dd, 1H, J=2.3 & 10.2 Hz), 6.86 (d, 2H, J=8.6 Hz), 7.13 (d, 2H, J=8.6 Hz), 7.28–7.60 (m, 10H).

Compound No. 213:

$^1$H-NMR (CDCl$_3$) δ: 0.91 (d, 1H, J=9.6 Hz), 1.99 (s, 3H), 3.81 (s, 3H), 4.54–4.56 (m, 1H), 4.69 & 4.75 (ABq, 2H, J=12.9 Hz), 4.76 (d, 1H, J=9.6 Hz), 5.51–5.52 (m, 1H), 5.77–5.89 (m, 2H), 7.28–7.59 (m, 10H).

EXAMPLE 15

The compounds of the formula (I) of the present invention listed in Table 11 were obtained in substantially the same manner as that described in Process 9.

The following are physiochemical data of the representative compounds listed in Table 11.

Compound No. 214:

$^1$H-NMR (DMSO-d$_6$) δ: 1.75 (s, 3H), 1.77 (s, 3H), 3.34 (s, 2H), 4.58 (s, 2H), 6.47 (s, 1H), 12.55 (brs, 1H).

Compound No. 215:

$^1$H-NMR (DMSO-d$_6$) δ: 1.57 (s, 3H), 1.63 (brs, 1H), 2.33–2.37 (m, 1H), 3.79 & 3.96 (ABq, 2H, J=16.8 Hz), 4.90 (d, 1H, J=6.9 Hz), 5.84 (d, 1H, J=6.9 Hz), 7.01–7.23 (m, 4H).

TABLE 11

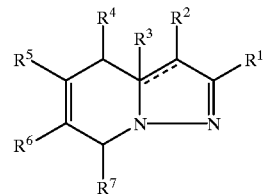

(I)

| Compound No. | R$^1$ | R$^2$ | R$^3$ | R$^4$ | R$^7$ | R$^5$ | R$^6$ |
|---|---|---|---|---|---|---|---|
| 214 | COOH | H | — | H | H | Me | Me |
| 215 | CONH$_2$ | OH | CONH$_2$ | H | H | Me | Me |
| 216 | CONH$_2$ | NH$_2$ | CONH$_2$ | 3-Py | 3-Py | H | H |
| 217 | COOH | H | — | Me | Me | H | H |
| 218 | CONH$_2$ | SH | CONH$_2$ | Ph-p-Cl | Ph-p-Cl | H | H |
| 219 | COOH | H | — | Ph-p-CN | Ph-p-CN | H | H |
| 220 | COOH | H | — | Ph-p-NO$_2$ | Ph-p-NO$_2$ | H | H |
| 221 | CONH$_2$ | OH | CONH$_2$ | Ph-p-OMe | Ph-p-OMe | H | H |

Pharmacological Test:

Cardioprotective Effect in Ischemia/Reperfusion Model of Isolated Rat Hearts:

Method:

(1): Preparation of Isolated Perfused Hearts:

Male Sprague-Dawley rats (300–500 g) were used. The rats were anesthetized using 40 mg/kg of sodium pentobarbital (i.p.) after treating with heparin (i.v. 1000 U/kg). The hearts were excised and moved quickly to a Langendorlf apparatus where they were perfused with Krebs-Henseleit bicarbonate buffer (118 mM of NaCl; 4.7 mM of KCl; 2.55 mM of CaCl$_2$; 1.18 mM of KH$_2$PO$_4$; 24.88 mM of NaHCO$_3$; 11.1 mM of glucose) bubbled with mixture gas of 95% oxygen and 5% carbon dioxide at a constant perfusion pressure (75 mmHg). The parameters of cardiac function were determined as follows.

The physiological saline-filled latex balloon was inserted into the left ventricle and connected to a pressure transducer for measurement of left ventricular pressure (LVP). The volume of the balloon was adjusted to produce an LV end-diastolic pressure at 5–10 mmHg. The heart rate was determined with a tachometer and coronary flow was determined with an extra-corporeal electromagnetic flow tube.

(2): Experimental Protocol:

For the equilibration, the hearts were perfused for initial 15–20 minutes. Then, treatment with the test compounds was begun 15 minutes before the onset of ischemia. Global ischemia was initiated by shutting off the perfusate flow and this was maintained for 25 minutes. The hearts were submerged in 37° C. buffer during ischemia. Reperfusion was then begun with the test compounds and the hearts were allowed to recover for 30 minutes. The cardiac function was measured before the treatment of the test compounds, before ischemia and after reperfusion. The hearts were treated with 10$^{-5}$ mol of the test compounds dissolved in 0.04% of dimethylsulfoxide (DMSO), in comparison with the vehicle, i.e., 0.04% of DMSO alone, in the perfusate.

(3): Evaluation of the Cardioprotective Effects of the Test Compounds:

The cardioprotective effects of the test compounds were evaluated on the basis of the extent of recovery of LVP after reperfusion for 30 minutes.

Results:

The following Table 12 shows the recovery of LVP by the test compounds, which is expressed as the percentage of left ventricular developed pressure (LVDP) against the LVP before ischemia as assumed to be 100%.

TABLE 12

| Compound No. | LVDP(%) |
|---|---|
| 29 | 44.2 |
| 31 | 85.1 |
| 35 | 50.6 |
| 48 | 72.4 |
| 50 | 69.8 |
| 51 | 55.0 |
| 52 | 49.3 |
| 53 | 60.0 |
| 81 | 56.2 |
| 82 | 61.5 |
| 94 | 73.5 |
| 124 | 84.0 |
| 139 | 62.5 |
| 173 | 61.0 |

The folowing Table 13 shows the percentage of LVDP for the test compounds as compared with that for propranolol as a reference compound, when the recovery by propranolol is assumed to be 100%.

TABLE 13

| Compound No. | LVDP(%) | Compound No. | LVDP(%) |
|---|---|---|---|
| propranolol | 100.0 | 174 | 53.4 |
| 103 | 20.2 | 185 | 38.4 |
| 104 | 65.8 | 186 | 68.5 |
| 105 | 13.3 | 187 | 16.4 |
| 115 | 41.8 | 190 | 28.7 |
| 125 | 47.2 | 193 | 70.0 |
| 126 | 97.5 | 196 | 34.1 |
| 132 | 27.9 | 197 | 14.2 |
| 133 | 27.8 | 199 | 124.7 |
| 164 | 50.6 | 203 | 32.2 |
| 166 | 42.8 | 204 | 32.1 |
| 169 | 39.0 | 205 | 64.7 |
| 171 | 102.4 | 209 | 51.1 |

Toxicity:

(1): Toxicological study was carried out by using a group of 10 male mice of ICR type weighing from 20 to 23 grams. Aqueous solutions of polyethylene glycol 400 containing 10% of Compounds (29), (31), (124), (171) and (199) of the present invention were administered subcutaneously to the mice, and the mice were subjected to observations for one week.

The results revealed that the mice to which the compounds of the present invention were administered in the amount of 10 ml/kg were alive without any abnormal findings.

(2): Acute toxicological study was carried out by using 4-week old male mice of ICR type. A 0.025 N HCl-phygiological saline solutions containing the compounds of the present invention were administered orally to the mice which had not been fed for 16 hours before the experiment. The gross behavior of the mice was observed for 14 days after administration. The $LD_{50}$ was determined by Litchwhield Wilcoxon method. The compounds listed in Tables 12 and 13 were tested. The $LD_{50}$s of all the test compounds were more than 100 mg/kg.

What is claimed is:

1. A diazabicyclo compound of the formula (I):

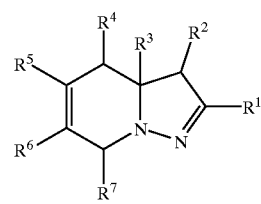

(I)

wherein $R^1$ is a group selected from the following:

(1) a lower alkyl group or lower alkenyl group which may be substituted by a cyano, nitro, lower alkylthio, lower alkylsulfinyl or lower alkylsulfonyl group, (2) a lower acyl group having an alkyl moiety of 1 to 4 carbon atoms which may be substituted by an imidazolyl, pyridyl, oxazolyl, thiazolyl, or thiadiazolyl group, (3) a 2-pyridyl, azetidinyl, pyrrolidinyl, imidazolyl, imidazolinyl, piperidinyl, pyrazolidinyl, tetrahydropyrimidinyl, morpholinyl, 1,3-oxazolin-2-yl, 1-oxa-2,4diazol-3-yl, 1,2,4-triazol-3-yl, thiazolidinyl, or 1-thia-3,5-diazolidin-2-yl group which may be substituted by a lower alkyl or lower alkoxycarbonyl group, and (4) a carbonyl group substituted by an imidazolyl, pyridyl, piperazinyl, oxazolyl, thiazolyl, or thiadiazolyl group, $R^2$ is a hydroxy group, $R^3$ is a lower alkoxycarbonyl group, $R^4$ and $R^7$, each of them being the same as the other, are hydrogen atoms or phenyl groups which may be substituted by a halogen, cyano, lower alkyl, lower alkoxy, nitro, aryl or lower acyl group having an alkyl moiety of 1 to 4 carbon atoms, and $R^5$ and $R^6$, each of them being the same as the other, are hydrogen atoms or lower alkyl groups, or a pharmaceutically acceptable salt thereof.

2. The diazabicyclo compound of claim 1 represented by the formula (I-b):

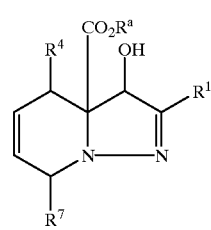

(I-b)

wherein $R^a$ is a lower alkyl group, and $R^1$, $R^4$ and $R^7$ are as defined in claim 1, or a pharmaceutically acceptable salt thereof.

3. The diazabicyclo compound of claim 1 represented by the formula (I-c):

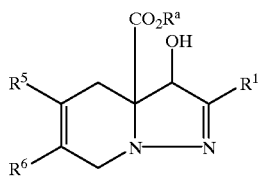

(I-c)

wherein $R^a$ is a lower alkyl group, and $R^1$, $R^5$ and $R^6$ are defined as in claim 1 or a pharmaceutically acceptable salt thereof.

4. The diazabicyclo compound of formula (I) of claim 1, wherein said lower acyl group having an alkyl moiety of 1 to 4 carbon atoms is an acetyl, propionyl, or butyryl group which may be substituted by an imidazolyl, pyridyl, oxazolyl, thiazolyl, or thiadiazolyl group.

5. The diazabicyclo compound of claim 4, wherein said pyridyl group is 2-pyridyl and $R^3$ is methoxycarbonyl.

6. The diazabicyclo compound of formula (I) of claim 1, wherein $R^1$ is a 2-pyridyl, azetidinyl, pyrrolidinyl, imidazolyl, imidazolinyl, piperidinyl, pyrazolidinyl, tetrahydropyrimidinyl, morpholinyl, 1,3-oxazolin-2-yl, 1-oxa-2,4-diazol-3-yl, 1,2,4-triazol-3-yl, thiazolidinyl, or 1-thia-3,5-diazolidin-2-yl group which may be substituted by a lower alkyl or lower alkoxycarbonyl group.

7. The diazabicyclo compound of formula (I) of claim 1, wherein $R^1$ is a carbonyl group substituted by an imidazolyl, pyridyl, piperazinyl, oxazolyl, thiazolyl, or thiadiazolyl group.

8. The diazabicyclo compound of formula (I) of claim 4, wherein $R^1$ is an acetyl substituted by a pyridyl group, $R^4$ and $R^7$ are phenyl groups, and $R^5$ and $R^6$ are hydrogen atoms.

9. A composition for use in treating cardiovascular disease, comprising an effective amount of the compound of formula (I) as claimed in claim 1, in admixture with a pharmaceutically acceptable carrier or excipient.

10. A composition for use in treating cardiovascular disease, comprising an effective amount of the compound according to any one of claims 2 or 3 in admixture with a pharmaceutically acceptable carrier or excipient.

11. A method of treating a cardiovascular disease, comprising the step of administering to a patient in need of treatment an effective amount of a compound of formula (I) according to claim 1, or a pharmaceutically acceptable salt thereof.

* * * * *